(12) United States Patent
Dillon et al.

(10) Patent No.: US 7,799,796 B2
(45) Date of Patent: *Sep. 21, 2010

(54) DIAMINOPYRIMIDINES AS P2X$_3$ AND P2X$_{2/3}$ MODULATORS

(75) Inventors: Michael Patrick Dillon, San Francisco, CA (US); Alam Jahangir, San Jose, CA (US); Clara Jeou Jen Lin, Palo Alto, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 918 days.

This patent is subject to a terminal disclaimer.

(21) Appl. No.: 11/509,890

(22) Filed: Aug. 25, 2006

(65) Prior Publication Data

US 2007/0049534 A1 Mar. 1, 2007

Related U.S. Application Data

(60) Provisional application No. 60/713,398, filed on Sep. 1, 2005.

(51) Int. Cl.
*C07D 239/48* (2006.01)
*C07D 413/12* (2006.01)
*A61K 31/506* (2006.01)

(52) U.S. Cl. ...................... 514/275; 544/325
(58) Field of Classification Search ............... 544/325; 514/275
See application file for complete search history.

(56) References Cited

U.S. PATENT DOCUMENTS

| | | | |
|---|---|---|---|
| 2,953,567 A | 9/1960 | Hitchings et al. |
| 3,715,357 A | 2/1973 | Rey-Bellet et al. |
| 3,849,470 A | 11/1974 | Cresswell et al. |
| 3,850,927 A | 11/1974 | Cresswell et al. |
| 3,852,276 A | 12/1974 | Cresswell et al. |
| 3,855,265 A | 12/1974 | Cresswell et al. |
| 3,931,181 A | 1/1976 | Kompis et al. |
| 3,940,393 A | 2/1976 | Greenspan et al. |
| 3,991,050 A | 11/1976 | Cresswell et al. |
| 4,024,145 A | 5/1977 | Kompis |
| 4,033,962 A | 7/1977 | Rosen |
| 4,039,543 A | 8/1977 | Kompis et al. |
| 4,052,553 A | 10/1977 | Cresswell et al. |
| 4,075,209 A | 2/1978 | Jernow et al. |
| 4,108,888 A | 8/1978 | Rosen |
| 4,115,650 A | 9/1978 | Manchand |
| 4,143,227 A | 3/1979 | Rosen |
| 4,144,263 A | 3/1979 | Yeowell et al. |
| 4,151,196 A | 4/1979 | Rosen |
| 4,189,581 A * | 2/1980 | Scharwaechter et al. .... 544/324 |
| 4,216,319 A | 8/1980 | Yeowell et al. |
| 4,232,023 A | 11/1980 | Dick et al. |
| 4,255,574 A | 3/1981 | Rosen |
| 4,258,045 A | 3/1981 | Poe et al. |
| 4,386,084 A | 5/1983 | Scharwaechter et al. |
| 4,415,574 A | 11/1983 | Laruelle et al. |
| 4,485,248 A | 11/1984 | Dall'Asta |
| 4,515,948 A | 5/1985 | Kompis et al. |
| 4,587,341 A | 5/1986 | Roth et al. |
| 4,590,271 A | 5/1986 | Daluge et al. |
| 4,883,798 A | 11/1989 | Petöcz et al. |
| 4,912,112 A | 3/1990 | Seydel et al. |
| 4,996,198 A | 2/1991 | Schildknecht et al. |
| 5,063,219 A | 11/1991 | Schildknecht et al. |
| 5,240,640 A | 8/1993 | Siiman et al. |
| 5,258,373 A | 11/1993 | Schildknecht et al. |
| 5,541,186 A | 7/1996 | Breu et al. |
| 6,136,971 A | 10/2000 | Harrington et al. |
| 6,211,185 B1 | 4/2001 | Strobel et al. |
| 6,410,543 B1 | 6/2002 | Strobel et al. |
| 6,423,720 B1 | 7/2002 | Gangjee |
| 6,583,148 B1 | 6/2003 | Kelley et al. |
| 2003/0040513 A1 | 2/2003 | Baxter et al. |
| 2005/0209260 A1 * | 9/2005 | Broka et al. ............. 514/275 |

FOREIGN PATENT DOCUMENTS

| | | |
|---|---|---|
| EP | 0 237 516 A1 | 9/1987 |
| EP | 0 658 548 B1 | 11/1997 |
| EP | 0 959 073 A1 | 11/1999 |
| EP | 0 743 307 B1 | 9/2001 |
| EP | 0 959 072 B1 | 9/2002 |
| EP | 1 310 493 A1 | 5/2003 |
| WO | WO 01/17976 A1 | 3/2001 |
| WO | WO 01/22938 A1 | 4/2001 |
| WO | WO 01/81335 A1 | 11/2001 |
| WO | WO 01/81338 A1 | 11/2001 |
| WO | WO 02/08200 A2 | 1/2002 |

(Continued)

OTHER PUBLICATIONS

Broka et al., CAPLUS Abstract 143:326390 (2005).*

(Continued)

*Primary Examiner*—Deepak Rao
(74) *Attorney, Agent, or Firm*—Robert C. Hall

(57) ABSTRACT

Compounds and methods for treating diseases mediated by a P2X$_3$ and/or a P2X$_{2/3}$ receptor antagonist, the compounds being of formula (I):

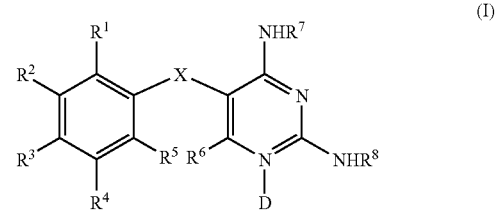

wherein D, X, R$^1$, R$^2$, R$^3$, R$^4$, R$^5$, R$^6$, R$^7$ and R$^8$ are as defined herein.

7 Claims, No Drawings

FOREIGN PATENT DOCUMENTS

| WO | WO 02/24665 A1 | 3/2002 |
| WO | WO 02/053557 A1 | 7/2002 |
| WO | WO 02/083650 A1 | 10/2002 |
| WO | WO 02/094767 A2 | 11/2002 |

OTHER PUBLICATIONS

Barnes, Frontrunners in novel pharmacotherapy of COPD, Current Opinion in Pharmacology, 2008, 8:300-307.*

Cazzola et al., Treating Systemic effects of COPD, TRENDS in Pharmacological Sciences, vol. 28, No. 10, pp. 544-550, 2007.*

Fox et al., Models of chronic obstructive pulmonary disease: a review of current status, Drug Discovery Today: Disease Models, vol. 1, No. 3, pp. 319-328 (2004).*

Bundgaard, Design of Prodrugs, p. 1, 1985.*

Silverman, Prodrugs and Drug Delivery Systems, Chapter 8, The Organic Chemistry of Drug Design and Drug Action, pp. 353-399, 1997.*

Calas, M., et al., "Synthesis of new trimethoprim analogs. Antibacterial structure-activity relationship," *Eur. J. Med. Chem*, 1982 17(6): 497-504.

Selassie, C.D., et al., "Quantitative structure-activity relationships of 2,4-diamino-5-(2-x-benzyl) pyrimidines versus bacterial and avian dihydrofolate reductase," *J. Med. Chemistry*, 1998 41(22): 4261-4272.

Dunn, S.M.J., et al., "Kinetics of ternary complex formation between dihydrofolate reductase, coenzyme, and inhibitors," *Biochemistry*, 1980, 19: 766-773.

Falco, E.A., et al., "5-Arylthiopyrimidines. 1. 2,4-diamino derivatives," *Journal of Organic Chemistry*, 1961, 26: 1143-1146.

Seiler, P., et al., "Partition coefficients of 5-(substituted benzyl)-2,4-diaminopyrimidines," *Arzneim.-Forsch*, 1982, 32 (7): 711-714.

* cited by examiner

DIAMINOPYRIMIDINES AS P2X$_3$ AND P2X$_{2/3}$ MODULATORS

CROSS REFERENCE TO RELATED APPLICATIONS

This application is entitled to the benefit of provisional patent application Ser. No. 60/713,398 filed on Sep. 1, 2005, the disclosure of which is incorporated herein by reference.

FIELD OF THE INVENTION

This invention pertains to compounds useful for treatment of diseases associated with P2X purinergic receptors, and more particularly to P2X$_3$ and/or P2X$_{2/3}$ antagonists usable for treatment of genitourinary, gastrointestinal, respiratory, and pain-related diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, P2X$_1$; P2X$_2$; P2X$_3$; P2X$_4$; P2X$_5$; and P2X$_7$; and three heteromeric receptors P2X$_{2/3}$, P2X$_{4/6}$, P2X$_{1/5}$ (See, e.g., Chen, et al. (1995) Nature 377:428-431; Lewis, et al. (1995) Nature 377:432-435; and Burnstock (1997) Neuropharmacol. 36:1127-1139). The structure and chromosomal mapping of mouse genomic P2X$_3$ receptor subunit has also been described (Souslova, et al. (1997) Gene 195:101-111). In vitro, co-expression of P2X$_2$ and P2X$_3$ receptor subunits is necessary to produce ATP-gated currents with the properties seen in some sensory neurons (Lewis, et al. (1995) Nature 377:432-435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). P2X$_3$ receptors have been identified on nociceptive neurons in the tooth pulp (Cook et al., Nature 387:505-508 (1997)). ATP released from damaged cells may thus lead to pain by activating P2X$_3$ and/or P2X$_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that P2X$_2$ and P2X$_3$ are involved in nociception, and that modulators of P2X receptors are potentially useful as analgesics.

Other researchers have shown that P2X$_3$ receptors are expressed in human colon, and are expressed at higher levels in inflamed colon than in normal colon (Y. Yiangou et al, Neurogastroenterol Mot (2001) 13:365-69). Other researchers have implicated the P2X$_3$ receptor in detection of distension or intraluminal pressure in the intestine, and initiation of reflex contractions (X. Bian et al., J Physiol (2003) 551.1:309-22), and have linked this to colitis (G. Wynn et al., Am J Physiol Gastrointest Liver Physiol (2004) 287:G647-57).

Inge Brouns et al. (Am J Respir Cell Mol Biol (2000) 23:52-61) found that P2X$_3$ receptors are expressed in pulmonary neuroepithelial bodies (NEBs), implicating the receptor in pain transmission in the lung. More recently, others have implicated P2X$_2$ and P2X$_3$ receptors in pO$_2$ detection in pulmonary NEBs (W. Rong et al., J Neurosci (2003) 23(36):11315-21).

There is accordingly a need for methods of treating diseases, conditions and disorders mediated by P2X$_3$ and/or P2X$_{2/3}$ receptors, as well as a need for compounds that act as modulators of P2X receptors, including antagonists of P2X$_3$ and P2X$_{2/3}$ receptors. The present invention satisfies these needs as well as others.

Chemical derivatization of active drug moieties is frequently undertaken for a variety of reasons including modification of the physical properties of the active drug, optimization of the pharmacokinetic parameters and site-specific targeting or localization of the active moiety to specific target tissues or cells. Albert introduced the term prodrug to describe a compound which lacks intrinsic biological activity but which is capable of metabolic transformation to the active drug substance (A. Albert, Selective Toxicity, Chapman and Hall, London, 1951). While the metabolic transformation can catalyzed by specific enzymes, often hydrolases, the active compound can also be released by non-specific chemical processes. Prodrugs have been recently reviewed (P. Ettmayer et al., J. Med Chem. 2004 47(10):2393-2404; K. Beaumont et al., Curr. Drug Metab. 2003 4:461-485; H. Bundgaard, Design of Prodrugs: Bioreversible derivatives for various functional groups and chemical entities in Design of Prodrugs, H. Bundgaard (ed) Elsevier Science Publishers, Amersterdam 1985).

SUMMARY OF THE INVENTION

The invention provides compound of formula (I):

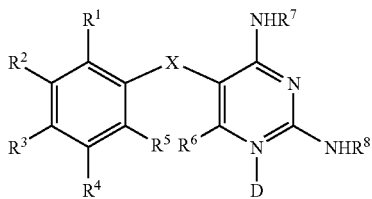

(I)

or a pharmaceutically acceptable salt thereof, wherein:

X is:
—CH$_2$—;
—O—;
—S(O)$_n$—;
or —NR$^c$—
wherein
n is from 0 to 2 and
R$^c$ is hydrogen or alkyl;
D is an optional oxygen;
R$^1$ is:
alkyl;
alkenyl;
alkynyl;
cycloalkyl;
cycloalkenyl;
halo;
haloalkyl; or
hydroxyalkyl;
R$^2$, R$^3$, R$^4$ and R$^5$ each independently is:
hydrogen;
alkyl;
aminosulfonyl;
alkenyl;
halo;
amido;
haloalkyl;
alkoxy;
hydroxy;
haloalkoxy;
nitro;
amino;
hydroxyalkyl;
alkoxyalkyl;
hydroxyalkoxy;
alkynylalkoxy;
alkylsulfonyl;
arylsulfonyl;
cyano;
aryl;
heteroaryl;
heterocyclyl;
heterocyclylalkoxy;
aryloxy;
heteroaryloxy;
aralkyloxy;
heteroaralkyloxy;
optionally substituted phenoxy;
—C≡C—R$^a$;
—(CH$_2$)$_m$-(Z)$_n$-(CO)—R$^b$;
—(CH$_2$)$_m$-(Z)$_n$-SO$_2$—(NR$^c$)$_n$—R$^b$
wherein
m and n each independently is 0 or 1,
Z is O or NR$^c$,
R$^a$ is hydrogen; alkyl; aryl; aralkyl; heteroaryl; heteroaralkyl; hydroxyalkyl; alkoxyalkyl; alkylsulfonylalkyl; aminoalkyl; cyanoalkyl; alkylsilyl, cycloalkyl, cycloalkylalkyl; heterocycyl; and heterocyclylalkyl;
R$^b$ is hydrogen, alkyl, hydroxy, alkoxy, amino, hydroxyalkyl or alkoxyalkyl, and
each R$^c$ is independently hydrogen or alkyl;
or R$^3$ and R$^4$ together with the atoms to which they are attached may form a five or six-membered ring that optionally includes one or two heteroatoms selected from O, S and N;
or R$^2$ and R$^3$ together with the atoms to which they are attached may form a five or six-membered ring that optionally includes one or two heteroatoms selected from O, S and N;
R$^6$ is:
hydrogen;
alkyl;
halo;
haloalkyl;
amino; or
alkoxy; and
one of R$^7$ and R$^8$ is hydrogen and the other is R$^9$, or both R$^7$ and R$^8$ are R$^9$:
each R$^9$ is independently:
—(C═O)—R$^d$;
—(O═)P(OR$^g$)$_2$;
—S(═O)$_2$OR$^g$; or
a mono-, di- or tri-peptide,
wherein
R$^d$ is alkyl, alkoxy, alkoxyalkyl, alkoxyalkoxyalkyl, alkylcarbonyloxyalkyl, amino, cycloalkyl, cycloalkylalkyl, aryl, arylalkyl, heteroaryl, heteroarylalkyl, heterocyclyl, cycloalkyloxy, cycloalkylalkyloxy, aryloxy, arylalkyloxy, heteroaryloxy, heteroarylalkyloxy, heterocyclyloxy, hydroxyalkyl, —(CH$_2$)$_p$—C(═O)—R$^e$, —(CH═CH)—C(═O)—R$^e$, or —CH(NH$_2$)—R$^f$;
wherein
R$^e$ is hydrogen, hydroxy, alkyl, alkoxy, amino, cycloalkyl, cycloalkylalkyl, aryl, arylalkyl, heteroaryl, heteroarylalkyl, heterocyclyl, cycloalkyloxy, cycloalkylalkyloxy, aryloxy, aryl alkyloxy, heteroaryloxy, heteroarylalkyloxy or heterocyclyloxy;
p is 2 or 3;
R$^f$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl; and
R$^g$ is hydrogen, alkyl, an alkali metal ion or an alkaline earth metal ion;

provided that when R$^1$ is isopropyl, R$^2$, R$^5$ and R$^6$ are hydrogen, R$^3$ is methoxy and R$^4$ is methyl or methoxy, then R$^d$ is not methyl.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of two to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxyalkyl" means a group of the formula —R—O—R'—O—R" wherein R and R' each are alkylene and R" is alkyl as defined herein.

"Alkylcarbonyloxyalkyl" means a group of the formula —R—O—C(O)—R' wherein R is alkylene and R' is alkyl as defined herein.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl means a moiety of the formula —R'—R"—R''' where where R' is alkylene, R" is —$SO_2$— and R''' is alkyl as defined herein.

"Alkylamino" means a moiety of the formula —NR—R' wherein R is hydrogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkali metal ion means a monovalent ion of a group Ia metal such as lithium, sodium, potassium, rubidium or cesium, preferably sodium or potassium.

"Alkaline earth metal ion" means a divalent ion of a group IIA metal such as berylium, magnesium, calcium, strontium or barium, preferably magnesium or calcium.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Aminosulfonyl" means a group —$SO_2$—NR'R" wherein R' and R" each independently is hydrogen or alkyl. "Aminosulfonyl" as used herein thus encompasses "alkylaminosulfonyl" and "dialkylaminosulfonyl".

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Cyanoalkyl"" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

Heteroarylalkyl" or "heteroaralkyl" means a group of the formula —R—R' wherein R is alkylene and R' is heteroaryl as defined herein.

"Heteroarylsulfonyl means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Peptide" means an amide derived from two or more amino acids by combination of the amino group of one acid with the carboxyl group. "Monopeptide" means a single amino acid, "dipeptide" means an amide compound comprising two amino acids, "tripeptide" means an amide compound comprising three amino acids, and so on. The C-terminus of a "peptide" may be joined to another moiety via an ester functionality.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl (including hydroxyalkyl), halo, nitro, cyano, hydroxy, alkoxy, amino, acylamino, mono-alkylamino, di-alkylamino, haloalkyl, haloalkoxy, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p 1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Respiratory disorder" or disease refers to, without limitation, chronic obstructive pulmonary disease (COPD), asthma, bronchospasm, and the like.

"Gastrointestinal disorder" ("GI disorder") or disease refers to, without limitation, Irritable Bowel Syndrome (IBS), Inflammatory Bowel Disease (IBD), biliary colic and other biliary disorders, renal colic, diarrhea-dominant IBS, pain associated with GI distension, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

All patents and publications identified herein are incorporated herein by reference in their entirety.

Compounds of the Invention

U.S. patent application Ser. No. 11/071,555 filed on Mar. 3, 2005 and incorporated herein by reference, disclose highly effective modulators of the $P2X_3$ and $P2X_{2/3}$ receptors and are useful in the treatment of $P2X_3$ and $P2X_{2/3}$-mediated diseases and conditions. This invention provides prodrug compounds of these $P2X_3$ and $P2X_{2/3}$ receptor modulators that achieve higher blood levels of active ingredient for more efficient dosing regimens in the treatment of $P2X_3$ and $P2X_{2/3}$-mediated diseases. The prodrug compounds of the invention surprisingly exhibit improved pharmacokinetic properties over the parent compounds.

Accordingly, the invention provides compounds of the formula I:

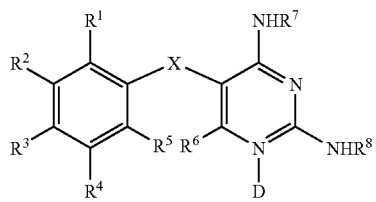

or a pharmaceutically acceptable salt thereof, wherein:

X is:
—CH$_2$—;
—O—;
—S(O)$_n$—;
or —NR$^c$—
wherein
n is from 0 to 2 and
R$^c$ is hydrogen or alkyl;

D is an optional oxygen;

R$^1$ is:
alkyl;
alkenyl;
alkynyl;
cycloalkyl;
cycloalkenyl;
halo;
haloalkyl; or
hydroxyalkyl;

R$^2$, R$^3$, R$^4$ and R$^5$ each independently is:
hydrogen;
alkyl;
aminosulfonyl;
alkenyl;
halo;
amido;
haloalkyl;
alkoxy;
hydroxy;
haloalkoxy;
nitro;
amino;
hydroxyalkyl;
alkoxyalkyl;
hydroxyalkoxy;
alkynylalkoxy;
alkylsulfonyl;
arylsulfonyl;
cyano;
aryl;
heteroaryl;
heterocyclyl;
heterocyclylalkoxy;
aryloxy;
heteroaryloxy;
aralkyloxy;
heteroaralkyloxy;
optionally substituted phenoxy;
—C≡C—R$^a$;
—(CH$_2$)$_m$-(Z)$_n$-(CO)—R$^b$;
—(CH$_2$)$_m$-(Z)$_n$-SO$_2$—(NR$^c$)$_n$—R$^b$
wherein
m and n each independently is 0 or 1,
Z is O or NR$^c$,
R$^a$ is hydrogen; alkyl; aryl; aralkyl; heteroaryl; heteroaralkyl; hydroxyalkyl; alkoxyalkyl; alkylsulfonylalkyl; aminoalkyl; cyanoalkyl; alkylsilyl; cycloalkyl; cycloalkylalkyl; heterocycyl; and heterocyclylalkyl;
R$^b$ is hydrogen, alkyl, hydroxy, alkoxy, amino, hydroxyalkyl or alkoxyalkyl, and
each R$^c$ is independently hydrogen or alkyl;
or R$^3$ and R$^4$ together with the atoms to which they are attached may form a five or six-membered ring that optionally includes one or two heteroatoms selected from O, S and N;
or R$^2$ and R$^3$ together with the atoms to which they are attached may form a five or six-membered ring that optionally includes one or two heteroatoms selected from O, S and N;

R$^6$ is:
hydrogen;
alkyl;
halo;
haloalkyl;
amino; or
alkoxy; and one of R$^7$ and R$^8$ is hydrogen and the other is R$^9$, or both R$^7$ and R$^8$ are R$^9$:

each R$^9$ is independently:
—(C═O)—R$^d$;
—(O═)P(OR$^g$)$_2$;
—S(═O)$_2$OR$^g$; or
a mono-, di- or tri-peptide,
wherein
R$^d$ is alkyl, alkoxy, alkoxyalkyl, alkoxyalkoxyalkyl, alkylcarbonyloxyalkyl, amino, cycloalkyl, cycloalkylalkyl, aryl, arylalkyl, heteroaryl, heteroarylalkyl, heterocyclyl, cycloalkyloxy, cycloalkylalkyloxy, aryloxy, arylalkyloxy, heteroaryloxy, heteroarylalkyloxy, heterocyclyloxy, hydroxyalkyl, —(CH$_2$)$_p$—C(═O)—R$^e$, —(CH═CH)—C(═O)—R$^e$, or —CH(NH$_2$)—R$^f$;
wherein
R$^e$ is hydrogen, hydroxy, alkyl, alkoxy, amino, cycloalkyl, cycloalkylalkyl, aryl, arylalkyl, heteroaryl, heteroarylalkyl, heterocyclyl, cycloalkyloxy, cycloalkylalkyloxy, aryloxy, arylalkyloxy, heteroaryloxy, heteroarylalkyloxy or heterocyclyloxy;
p is 2 or 3;
R$^f$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl; and
R$^g$ is hydrogen, alkyl, an alkali metal ion or an alkaline earth metal ion;

provided that when R$^1$ is isopropyl, R$^2$, R$^5$ and R$^6$ are hydrogen, R$^3$ is methoxy and R$^4$ is methyl or methoxy, then R$^d$ is not methyl.

In many embodiments of formula I, X is —O— or —CH$_2$—.

In many embodiments of formula I, D is absent.

In certain embodiments of formula I, R$^1$ is ethyl, isopropyl, iodo, ethynyl or cyclopropyl. In such embodiments R$^1$ may be isopropyl, iodo or ethynyl.

In certain embodiments of formula I, R$^5$ and R$^6$ are hydrogen.

In certain embodiments of formula I, R$^2$ is hydrogen.

In certain embodiments of formula I, R$^3$ and R$^4$ each independently is hydrogen, alkyl, alkenyl, halo, haloalkyl, alkoxy, hydroxy, haloalkoxy, alkylsulfonyl, heteroaryl, cyano, or —C≡C—R$^a$.

In certain embodiments of formula I, R$^3$ and R$^4$ each independently is hydrogen, halo, alkoxy, hydroxy, haloalkoxy, heteroaryl, alkylsulfonyl or —C≡C—R$^a$.

In certain embodiments of formula I, R$^3$ and R$^4$ each independently is halo, alkoxy, hydroxy, haloalkoxy, alkylsulfonyl heteroaryl or —C≡C—R$^a$.

In certain embodiments of formula I, R$^3$ is alkoxy and R$^4$ is halo, alkylsulfonyl, heteroaryl or —C≡C—R$^a$.

In certain embodiments of formula I, each R$^d$ independently is alkyl, alkoxy or —CH(NH$_2$)—R$^f$.

In certain embodiments of formula I, each R$^d$ independently is alkyl or alkoxy.

In certain embodiments of formula I, R$^7$ is hydrogen, R$^8$ is R$^9$, R$^9$ is —(C═O)—R$^d$, and R$^d$ is alkyl or alkoxy.

In certain embodiments of formula I, R$^8$ is hydrogen, R$^7$ is R$^9$, R$^9$ is —(C═O)—R$^d$, and R$^d$ is alkyl or alkoxy.

In certain embodiments of formula I, R$^7$ and R$^8$ are R$^9$, R$^9$ is —(C═O)—R$^d$, and each R$^d$ is independently alkyl or alkoxy.

In certain embodiments of formula I, R$^7$ is hydrogen, R$^8$ is R$^9$, R$^9$ is —(C═O)—R$^d$, and R$^d$ is heteroaryl.

In certain embodiments of formula I, R$^8$ is hydrogen, R$^7$ is R$^9$, R$^9$ is —(C═O)—R$^d$, and R$^d$ is heteroaryl. Preferred heteroaryl in such embodiments include pyridinyl, pyrimidinyl, pyrazinyl, pyridazinyl, pyrrolyl, imidazolyl, thienyl or furanyl, each of which may be optionally substituted.

In certain embodiments of formula I, R$^7$ and R$^8$ are R$^9$, R$^9$ is —(C═O)—R$^d$, and each R$^d$ is heteroaryl.

In certain embodiments of formula I, R$^7$ is hydrogen, R$^8$ is R$^9$, R$^9$ is —(C═O)—R$^d$, and R$^d$ is heterocyclyl.

In certain embodiments of formula I, R$^8$ is hydrogen, R$^7$ is R$^9$, R$^9$ is —(C═O)—R$^d$, and R$^d$ is heterocyclyl.

In certain embodiments of formula I, R$^7$ and R$^8$ are R$^9$, R$^9$ is —(C═O)—R$^d$, and each R$^d$ is heterocyclyl.

In certain embodiments of formula I, X is O or —CH$_2$—, R$^1$ is ethyl, isopropyl, iodo, ethynyl or cyclopropyl and R$^2$, R$^5$ and R$^6$ are hydrogen.

In certain embodiments of formula I, X is O or —CH$_2$—, R$^1$ is ethyl, isopropyl, iodo, ethynyl or cyclopropyl, R$^2$, R$^5$ and R$^6$ are hydrogen, and R$^3$ and R$^4$ each independently is hydrogen, alkyl, alkenyl, halo, haloalkyl, alkoxy, hydroxy, haloalkoxy, alkylsulfonyl, heteroaryl, cyano, or —C≡C—R$^a$.

In certain embodiments of formula I, X is O or —CH$_2$—, R$^1$ is ethyl, isopropyl, iodo, ethynyl or cyclopropyl, R$^2$, R$^5$ and R$^6$ are hydrogen, R$^3$ is hydrogen, halo, alkoxy, hydroxy or haloalkoxy, and R$^4$ is halo, heteroaryl, alkylsulfonyl, cyano; or —C≡C—R$^a$.

In certain embodiments of formula I, X is O or —CH$_2$—, R$^1$ is ethyl, isopropyl, iodo, ethynyl or cyclopropyl, R$^2$, R$^5$ and R$^6$ are hydrogen, R$^3$ is hydrogen, halo, alkoxy, hydroxy or haloalkoxy, R$^4$ is halo, heteroaryl, alkylsulfonyl, cyano; or —C≡C—R$^a$, one of R$^7$ and R$^8$ is hydrogen and the other is R$^9$, R$^9$ is —(C═O)—R$^d$, and R$^d$ is alkyl, alkoxy or —CH(NH$_2$)—R$^f$.

In certain embodiments of formula I, X is O, R$^1$ is isopropyl, iodo or ethynyl, R$^2$, R$^5$ and R$^6$ are hydrogen, R$^3$ is methoxy, R$^4$ is iodo or —C≡CH, one of R$^7$ and R$^8$ is hydrogen and the other is R$^9$, R$^9$ is —(C═O)—R$^d$, and R$^d$ is alkyl or alkoxy.

In certain embodiments of formula I, X is O, R$^1$ is isopropyl, iodo or ethynyl, R$^2$, R$^5$ and R$^6$ are hydrogen, R$^3$ is methoxy, R$^4$ is iodo or —C≡CH, R$^7$ and R$^8$ are R$^9$, R$^9$ is —(C═O)—R$^d$, and each R$^d$ is independently alkyl or alkoxy.

In certain embodiments of formula I, X is O, R$^1$ is isopropyl, R$^2$, R$^5$ and R$^6$ are hydrogen, R$^3$ is methoxy, R$^4$ is iodo or —C≡CH, one of R$^7$ and R$^8$ is hydrogen and the other is R$^9$, R$^9$ is —(C═O)—R$^d$, and R$^d$ is alkyl, alkoxy, heteroaryl or heterocyclyl.

In certain embodiments of formula I, X is O, R$^1$ is isopropyl, R$^2$, R$^5$ and R$^6$ are hydrogen, R$^3$ is methoxy, R$^4$ is iodo or —C≡CH, R$^7$ and R$^8$ are R$^9$, R$^9$ is —(C═O)—R$^d$, and each R$^d$ is independently alkyl, alkoxy, heteroaryl or heterocyclyl.

In certain embodiments of formula I, X is O, R$^2$, R$^5$ and R$^6$ are hydrogen, R$^3$ is alkoxy, R$^4$ is halo or —C≡CH, one of R$^7$ and R$^8$ is hydrogen and the other is R$^9$, R$^9$ is —(C═O)—R$^d$, and R$^d$ is alkyl, alkoxy, heteroaryl or heterocyclyl.

In certain embodiments of the invention, the subject compounds are more specifically of formula II:

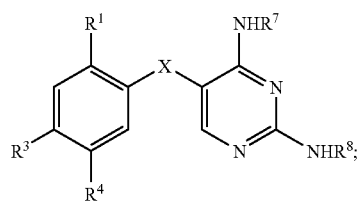

(II)

wherein X, R$^1$, R$^3$, R$^4$, R$^7$ and R$^8$ are as defined herein.

In many embodiments of formula II, X is —O— or —CH$_2$—. In certain of such embodiments, X is —O—.

In certain embodiments of formula II, R$^1$ is ethyl, isopropyl, iodo, ethynyl or cyclopropyl. In such embodiments R$^1$ may be isopropyl, iodo or ethynyl.

In certain embodiments of formula II, R$^3$ and R$^4$ each independently is hydrogen, alkyl, alkenyl, halo, haloalkyl, alkoxy, hydroxy, haloalkoxy, alkylsulfonyl, heteroaryl, cyano; or —C≡C—R$^a$.

In certain embodiments of formula II, R$^3$ and R$^4$ each independently is hydrogen, halo, alkoxy, hydroxy, haloalkoxy, heteroaryl, alkylsulfonyl or —C≡C—R$^a$.

In certain embodiments of formula II, R$^3$ and R$^4$ each independently is halo, alkoxy, hydroxy, haloalkoxy, alkylsulfonyl heteroaryl or —C≡C—R$^a$.

In certain embodiments of formula II, R$^3$ is alkoxy and R$^4$ is halo, alkylsulfonyl, heteroaryl or —C≡C—R$^a$.

In certain embodiments of formula II, each R$^d$ independently is alkyl, alkoxy or —CH(NH$_2$)—R$^f$.

In certain embodiments of formula II, each R$^d$ independently is alkyl or alkoxy.

In certain embodiments of formula II, R$^7$ is hydrogen, R$^8$ is R$^9$, R$^9$ is —(C═O)—R$^d$, and R$^d$ is alkyl or alkoxy.

In certain embodiments of formula II, $R^8$ is hydrogen, $R^7$ is $R^9$, $R^9$ is —(C=O)—$R^d$, and $R^d$ is alkyl or alkoxy.

In certain embodiments of formula II, $R^7$ and $R^8$ are $R^9$, each $R^9$ is —(C=O)—$R^d$, and each $R^d$ is independently alkyl or alkoxy.

In certain embodiments of formula II, X is O or —CH$_2$— and $R^1$ is ethyl, isopropyl, iodo, ethynyl or cyclopropyl.

In certain embodiments of formula II, X is O or —CH$_2$—, $R^1$ is ethyl, isopropyl, iodo, ethynyl or cyclopropyl and $R^3$ and $R^4$ each independently is hydrogen, alkyl, alkenyl, halo, haloalkyl, alkoxy, hydroxy, haloalkoxy, alkylsulfonyl, heteroaryl, cyano, or —C≡C—$R^a$.

In certain embodiments of formula II, X is O or —CH$_2$—, $R^1$ is ethyl, isopropyl, iodo, ethynyl or cyclopropyl, $R^3$ is hydrogen, halo, alkoxy, hydroxy or haloalkoxy, and $R^4$ is halo, heteroaryl, alkylsulfonyl, cyano, or —C≡C—$R^a$.

In certain embodiments of formula II, X is O or —CH$_2$—, $R^1$ is ethyl, isopropyl, iodo, ethynyl or cyclopropyl, $R^3$ is hydrogen, halo, alkoxy, hydroxy or haloalkoxy, $R^4$ is halo, heteroaryl, alkylsulfonyl, cyano; or —C≡C—$R^a$, one of $R^7$ and $R^8$ is hydrogen and the other is $R^9$, $R^9$ is —(C=O)—$R^d$, and $R^d$ is alkyl or alkoxy.

In certain embodiments of formula II, X is O, $R^1$ is isopropyl, iodo or ethynyl, $R^3$ is methoxy, $R^4$ is iodo or —C≡CH, one of $R^7$ and $R^8$ is hydrogen and the other is $R^9$, $R^9$ is —(C=O)—$R^d$, and $R^d$ is alkyl or alkoxy.

In certain embodiments of formula II, X is O, $R^1$ is isopropyl, $R^3$ is methoxy, $R^4$ is iodo or —C≡CH, one of $R^7$ and $R^8$ is hydrogen and the other is $R^9$, $R^9$ is —(C=O)—$R^d$, and $R^d$ is alkyl, alkoxy, heteroaryl or heterocyclyl.

In certain embodiments of formula II, $R^7$ is hydrogen, $R^8$ is $R^9$, $R^9$ is —(C=O)—$R^d$, and $R^d$ is heteroaryl.

In certain embodiments of formula II, $R^8$ is hydrogen, $R^7$ is $R^9$, $R^9$ is —(C=O)—$R^d$, and $R^d$ is heteroaryl.

In certain embodiments of formula II, $R^7$ and $R^8$ are $R^9$, $R^9$ is —(C=O)—$R^d$, and each $R^d$ is heteroaryl.

In certain embodiments of formula II, $R^7$ is hydrogen, $R^8$ is $R^9$, $R^9$ is —(C=O)—$R^d$, and $R^d$ is heterocyclyl.

In certain embodiments of formula II, $R^8$ is hydrogen, $R^7$ is $R^9$, $R^9$ is —(C=O)—$R^d$, and $R^d$ is heterocyclyl.

In certain embodiments of formula II, $R^7$ and $R^8$ are $R^9$, $R^9$ is —(C=O)—$R^d$, and each $R^d$ is heterocyclyl.

In certain embodiments the compounds of the invention are of formula III:

$$\text{(III)}$$

wherein $R^1$, $R^3$, $R^4$, $R^7$ and $R^8$ are as defined herein.

In certain embodiments of formula III, $R^1$ is ethyl, isopropyl, iodo, ethynyl or cyclopropyl. In such embodiments $R^1$ may be isopropyl, iodo or ethynyl. Preferably, $R^1$ is isopropyl.

In certain embodiments of formula III, $R^3$ and $R^4$ each independently is hydrogen, alkyl, alkenyl, halo, haloalkyl, alkoxy, hydroxy, haloalkoxy, alkylsulfonyl, heteroaryl, cyano; or —C≡C—$R^a$.

In certain embodiments of formula III, $R^3$ and $R^4$ each independently is hydrogen, halo, alkoxy, hydroxy, haloalkoxy, heteroaryl, alkylsulfonyl or —C≡C—$R^a$.

In certain embodiments of formula III, $R^3$ and $R^4$ each independently is halo, alkoxy, hydroxy, haloalkoxy, alkylsulfonyl heteroaryl or —C≡C—$R^a$.

In certain embodiments of formula III, $R^3$ is alkoxy and $R^4$ is halo, alkylsulfonyl, heteroaryl or —C≡C—$R^a$.

In certain embodiments of formula III, each $R^d$ independently is alkyl, alkoxy or —CH(NH$_2$)—$R^f$.

In certain embodiments of formula III, each $R^d$ independently is alkyl or alkoxy.

In certain embodiments of formula III, $R^7$ is hydrogen, $R^8$ is $R^9$, $R^9$ is —(C=O)—$R^d$, and $R^d$ is alkyl or alkoxy.

In certain embodiments of formula III, $R^8$ is hydrogen, $R^7$ is $R^9$, $R^9$ is —(C=O)—$R^d$, and $R^d$ is alkyl or alkoxy.

In certain embodiments of formula III, $R^7$ and $R^8$ are $R^9$, each $R^9$ is —(C=O)—$R^d$, and each $R^d$ is independently alkyl or alkoxy.

In certain embodiments of formula III, $R^1$ is ethyl, isopropyl, iodo, ethynyl or cyclopropyl and $R^3$ and $R^4$ each independently is hydrogen, alkyl, alkenyl, halo, haloalkyl, alkoxy, hydroxy, haloalkoxy, alkylsulfonyl, heteroaryl, cyano, or —C≡C—$R^a$.

In certain embodiments of formula III, $R^1$ is ethyl, isopropyl, iodo, ethynyl or cyclopropyl, $R^3$ is hydrogen, halo, alkoxy, hydroxy or haloalkoxy, and $R^4$ is halo, heteroaryl, alkylsulfonyl, cyano, or —C≡C—$R^a$.

In certain embodiments of formula III, $R^1$ is ethyl, isopropyl, iodo, ethynyl or cyclopropyl, $R^3$ is hydrogen, halo, alkoxy, hydroxy or haloalkoxy, $R^4$ is halo, heteroaryl, alkylsulfonyl, cyano, or —C≡C—$R^a$, one of $R^7$ and $R^8$ is hydrogen and the other is $R^9$, $R^9$ is —(C=O)—$R^d$, and $R^d$ is alkyl or alkoxy.

In certain embodiments of formula III, $R^1$ is isopropyl, iodo or ethynyl, $R^3$ is methoxy, $R^4$ is iodo or —C≡CH, one of $R^7$ and $R^8$ is hydrogen and the other is $R^9$, $R^9$ is —(C=O)—$R^d$, and $R^d$ is alkyl or alkoxy.

In certain embodiments of formula III, $R^1$ is isopropyl, $R^3$ is methoxy, $R^4$ is iodo or —C≡CH, one of $R^7$ and $R^8$ is hydrogen and the other is $R^9$, $R^9$ is —(C=O)—$R^d$, and $R^d$ is heteroaryl.

In certain embodiments of formula III, $R^1$ is isopropyl, $R^3$ is methoxy, $R^4$ is iodo or —C≡CH, one of $R^7$ and $R^8$ is hydrogen and the other is $R^9$, $R^9$ is —(C=O)—$R^d$, and $R^d$ is heterocyclyl.

In certain embodiments of formula III, $R^7$ is hydrogen, $R^8$ is $R^9$, $R^9$ is —(C=O)—$R^d$, and $R^d$ is heteroaryl.

In certain embodiments of formula III, $R^8$ is hydrogen, $R^7$ is $R^9$, $R^9$ is —(C=O)—$R^d$, and $R^d$ is heteroaryl.

In certain embodiments of formula III, $R^7$ and $R^8$ are $R^9$, $R^9$ is —(C=O)—$R^d$, and each $R^d$ is heteroaryl.

In certain embodiments of formula III, $R^7$ is hydrogen, $R^8$ is $R^9$, $R^9$ is —(C=O)—$R^d$, and $R^d$ is heterocyclyl.

In certain embodiments of formula III, $R^8$ is hydrogen, $R^7$ is $R^9$, $R^9$ is —(C=O)—$R^d$, and $R^d$ is heterocyclyl.

In certain embodiments of formula III, $R^7$ and $R^8$ are $R^9$, $R^9$ is —(C=O)—$R^d$, and each $R^d$ is heterocyclyl.

In certain embodiments of the invention the subject compounds are of formula IV:

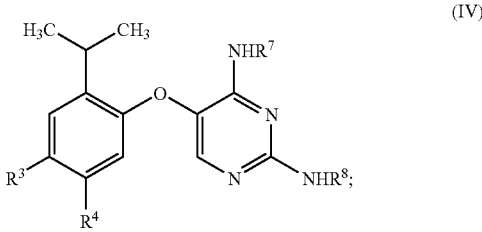

wherein $R^3$, $R^4$, $R^7$ and $R^8$ are as defined herein.

In certain embodiments of formulae IV, $R^3$ and $R^4$ each independently is hydrogen, alkyl, alkenyl, halo, haloalkyl, alkoxy, hydroxy, haloalkoxy, alkylsulfonyl, heteroaryl, cyano; or —C≡C—$R^a$.

In certain embodiments of formula IV, $R^3$ and $R^4$ each independently is hydrogen, halo, alkoxy, hydroxy, haloalkoxy, heteroaryl, alkylsulfonyl or —C≡C—$R^a$.

In certain embodiments of formula IV, $R^3$ and $R^4$ each independently is halo, alkoxy, hydroxy, haloalkoxy, alkylsulfonyl heteroaryl or —C≡C—$R^a$.

In certain embodiments of formula IV, $R^3$ is alkoxy and $R^4$ is halo, alkylsulfonyl, heteroaryl or —C≡C—$R^a$.

In certain embodiments of formula IV, $R^3$ is methoxy and $R^4$ is iodo

In certain embodiments of formula IV, each $R^d$ independently is alkyl, alkoxy or —CH(NH$_2$)—$R^f$.

In certain embodiments of formula IV, each $R^d$ independently is alkyl or alkoxy.

In certain embodiments of formula IV, $R^7$ is hydrogen, $R^8$ is —(C=O)—$R^d$, and $R^d$ is alkyl or alkoxy.

In certain embodiments of formula IV, $R^8$ is hydrogen, $R^7$ is —(C=O)—$R^d$, and $R^d$ is alkyl or alkoxy.

In certain embodiments of formula IV, $R^7$ and $R^8$ are —(C=O)—$R^d$, and each $R^d$ is independently alkyl or alkoxy.

In certain embodiments of formula IV, $R^3$ is hydrogen, halo, alkoxy, hydroxy or haloalkoxy, and $R^4$ is halo, heteroaryl, alkylsulfonyl, cyano, or —C≡C—$R^a$.

In certain embodiments of formula IV, $R^3$ is hydrogen, halo, alkoxy, hydroxy or haloalkoxy, $R^4$ is halo, heteroaryl, alkylsulfonyl, cyano, or —C≡C—$R^a$, one of $R^7$ and $R^8$ is hydrogen and the other is $R^9$, $R^9$ is —(C=O)—$R^d$, and each $R^d$ independently is alkyl or alkoxy.

In certain embodiments of formula IV, $R^3$ is methoxy, $R^4$ is iodo or —C≡CH, one of $R^7$ and $R^8$ is hydrogen and the other is $R^9$, $R^9$ is —(C=O)—$R^d$, and each $R^d$ independently is alkyl, alkoxy, heteroaryl or heterocyclyl.

In certain embodiments of formula IV, $R^7$ is hydrogen, $R^8$ is $R^9$, $R^9$ is —(C=O)—$R^d$, and $R^d$ is heteroaryl.

In certain embodiments of formula IV, $R^8$ is hydrogen, $R^7$ is $R^9$, $R^9$ is —(C=O)—$R^d$, and $R^d$ is heteroaryl.

In certain embodiments of formula IV, $R^7$ and $R^8$ are $R^9$, $R^9$ is —(C=O)—$R^d$, and each $R^d$ is heteroaryl.

In certain embodiments of formula IV, $R^7$ is hydrogen, $R^8$ is $R^9$, $R^9$ is —(C=O)—$R^d$, and $R^d$ is heterocyclyl.

In certain embodiments of formula IV, $R^8$ is hydrogen, $R^7$ is $R^9$, $R^9$ is —(C=O)—$R^d$, and $R^d$ is heterocyclyl.

In certain embodiments of formula IV, $R^7$ and $R^8$ are $R^9$, $R^9$ is —(C=O)—$R^d$, and each $R^d$ is heterocyclyl.

The invention also provides a method of using a compound of formula I as a prodrug for a compound of formula V

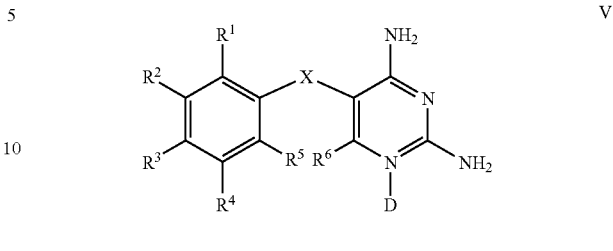

wherein D, X, $R^1$, $R^2$, $R^3$, $R^4$, $R^5$ and $R^6$ are as defined herein, the method comprising administering to a subject in need thereof an effective amount of a compound of formula I.

Where any of $R^1$, $R^2$, $R^3$, $R^4$, $R^5$, $R^6$, $R^7$, $R^8$, $R^a$, $R^b$, $R^c$, $R^d$, $R^e$, $R^f$, $R^g$, or $R^h$ is alkyl or contains an alkyl moiety, such alkyl is preferably lower alkyl, i.e. $C_1$-$C_6$alkyl, and more preferably $C_1$-$C_4$alkyl.

In embodiments of the invention where $R^d$ is heterocyclyl, preferred heterocyclyl include tetrahydropyranyl, piperidinyl, piperazinyl, morpholinyl, pyrrolidinyl and tetrahydrofuranyl, each of which may be optionally substituted. Particularly preferred heterocyclyl include tetrahydropyran-4-yl, 1-methyl-piperidin-4-yl, morpholin-4-yl, pyrrolidin-2-yl, pyrrolidin-1-yl, 4-hydroxypiperidin-1-yl, 4-(N,N-dimethyl)-piperidin-1-yl, 1-acetyl-pyrrolidin-2-yl, tetrahydrofuran-2-yl, 4-methyl-piperazin-1-yl, and 1-acetyl-piperidin-4-yl.

In embodiments of the invention where $R^d$ is heteroaryl, preferred heteroaryl include pyridinyl, pyrimidinyl, pyrazinyl, pyridazinyl, pyrrolyl, imidazolyl, thienyl or furanyl, each of which may be optionally substituted. Particularly preferred heteroaryl include pyridin-2-yl, pyridin-3-yl, pyridin-4-yl, pyrazin-2-yl, 5-methyl-pyrazin-2-yl, pyridazin-4-yl, imidazol-4-yl, 1-methyl-pyrazol-2-yl and furan-2-yl.

In embodiments where $R^4$ is heteroaryl or $R^a$ is heteroaryl, such heteroaryl is preferably thienyl, furanyl, imidazolyl, pyrazolyl, pyrrolyl, oxazolyl, thiazolyl, pyridyl or pyrimidinyl, each of which may be optionally substituted. In such embodiments $R^4$ and $R^a$ may be heteroaryl selected from thienyl, furanyl, imidazolyl, pyrazolyl, pyrrolyl, oxazolyl or thiazolyl, each optionally substituted. In other of such embodiments, $R^4$ and $R^a$ may be heteroaryl selected from thienyl, imidazolyl and oxazolyl, each optionally substituted.

The invention also provides methods for treating a disease mediated by a P2X$_3$ receptor antagonist, a P2X$_{2/3}$ receptor antagonist, or both, the method comprising administering to a subject in need thereof an effective amount of a compound of any of formulas (I) through (VIII). The disease may be genitourinary disease or urinary tract disease. In other instances the disease may be a disease is associated with pain. The urinary tract disease may be: reduced bladder capacity; frequency micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitis; pelvic pain syndrome; prostatodynia; cystitis; or idiopathic bladder hypersensitivity. The disease associated with pain may be: inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome. The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

Representative compounds in accordance with the methods of the invention are shown in Table 1.

TABLE 1

| # | Structure | Name (Autonom ™) | Mp (° C.) or M + H |
|---|---|---|---|
| 1 | 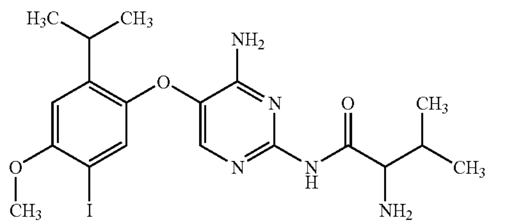 | 2-Amino-N-[4-amino-5-(5-iodo-2-isopropyl-4-methoxy-phenoxy)-pyrimidin-2-yl]-3-methyl-butyramide | 500 |
| 2 | 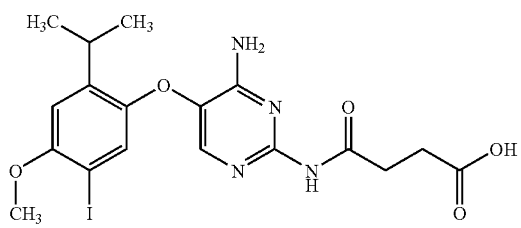 | N-[4-Amino-5-(5-iodo-2-isopropyl-4-methoxy-phenoxy)-pyrimidin-2-yl]-succinamic acid | 501 |
| 3 | 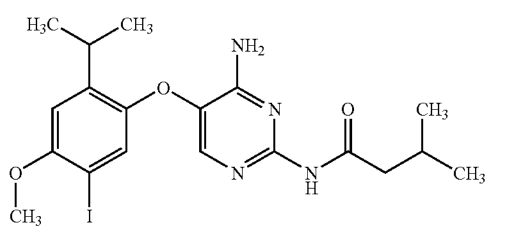 | N-[4-Amino-5-(5-iodo-2-isopropyl-4-methoxy-phenoxy)-pyrimidin-2-yl]-3-methyl-butyramide | 485 |
| 4 | 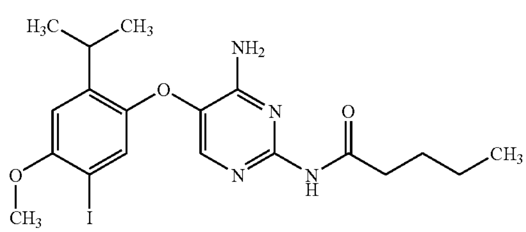 | Pentanoic acid [4-amino-5-(5-iodo-2-isopropyl-4-methoxy-phenoxy)-pyrimidin-2-yl]-amide | 485 |
| 5 | 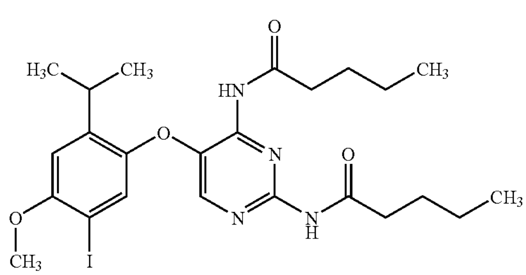 | Pentanoic acid [5-(5-iodo-2-isopropyl-4-methoxy-phenoxy)-4-pentanoylamino-pyrimidin-2-yl]-amide | 569 |

TABLE 1-continued

| # | Structure | Name (Autonom™) | Mp (° C.) or M + H |
|---|---|---|---|
| 6 | 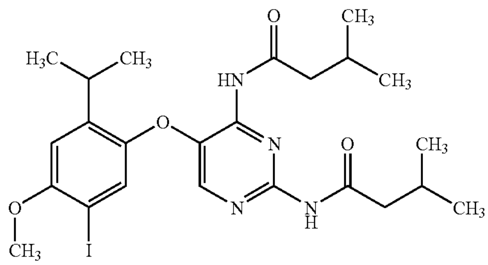 | N-[5-(5-Iodo-2-isopropyl-4-methoxy-phenoxy)-4-(3-methyl-butyrylamino)-pyrimidin-2-yl]-3-methyl-butyramide | 569 |
| 7 | 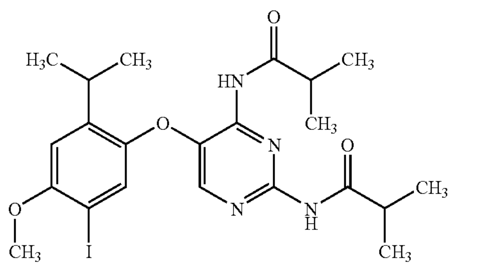 | N-[5-(5-Iodo-2-isopropyl-4-methoxy-phenoxy)-4-isobutyrylamino-pyrimidin-2-yl]-isobutyramide | 541 |
| 8 | 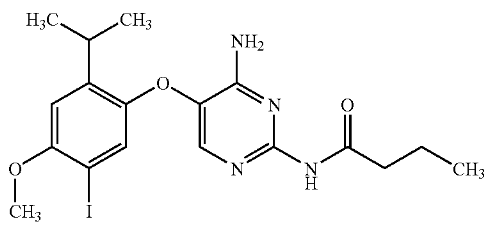 | N-[4-Amino-5-(5-iodo-2-isopropyl-4-methoxy-phenoxy)-pyrimidin-2-yl]-butyramide | 471 |
| 9 | 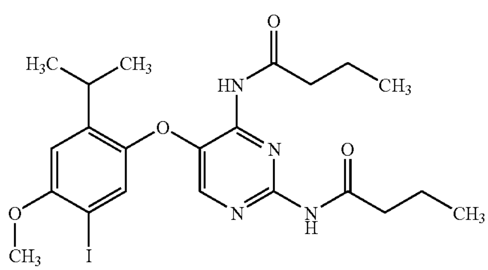 | N-[4-Butyrylamino-5-(5-iodo-2-isopropyl-4-methoxy-phenoxy)-pyrimidin-2-yl]-butyramide | 541 |
| 10 | 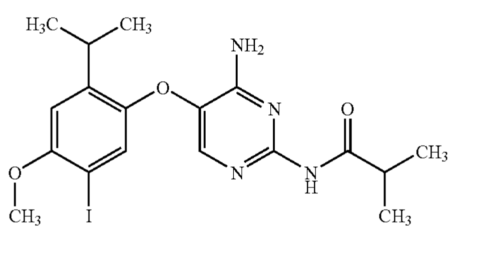 | N-[4-Amino-5-(5-iodo-2-isopropyl-4-methoxy-phenoxy)-pyrimidin-2-yl]-isobutyramide | 471 |
| 11 | 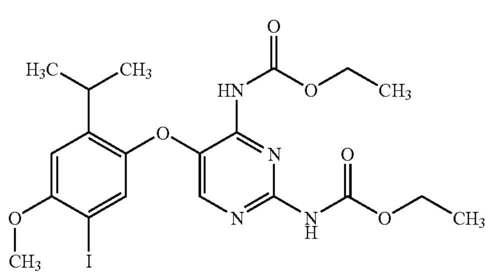 | [2-Ethoxycarbonylamino-5-(5-iodo-2-isopropyl-4-methoxy-phenoxy)-pyrimidin-4-yl]-carbamic acid ethyl ester | 545 |

TABLE 1-continued

| # | Structure | Name (Autonom ™) | Mp (° C.) or M + H |
|---|---|---|---|
| 12 | 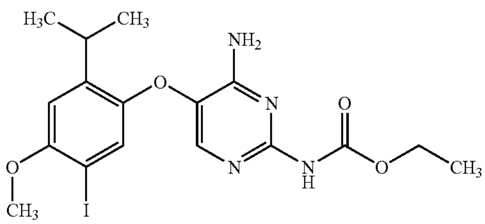 | [4-Amino-5-(5-iodo-2-isopropyl-4-methoxy-phenoxy)-pyrimidin-2-yl]-carbamic acid ethyl ester | 473 |
| 13 | 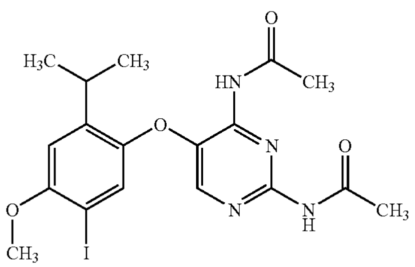 | N-[4-Acetylamino-5-(5-iodo-2-isopropyl-4-methoxy-phenoxy)-pyrimidin-2-yl]-acetamide | 485 |
| 14 | 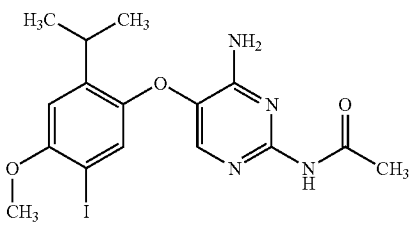 | N-[4-Amino-5-(5-iodo-2-isopropyl-4-methoxy-phenoxy)-pyrimidin-2-yl]-acetamide | 192.0-194.1° C. |
| 15 | 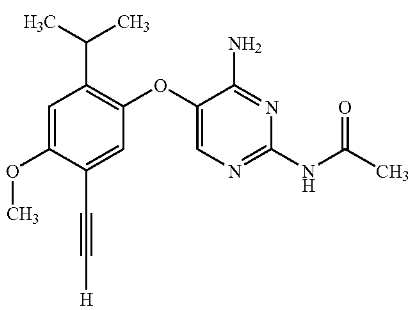 | N-[4-Amino-5-(5-ethynyl-2-isopropyl-4-methoxy-phenoxy)-pyrimidin-2-yl]-acetamide | 205.1-206.8° C. |
| 16 | 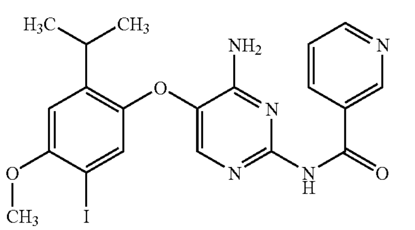 | N-[4-Amino-5-(5-iodo-2-isopropyl-4-methoxy-phenoxy)-pyrimidin-2-yl]-nicotinamide | 506 |
| 17 | 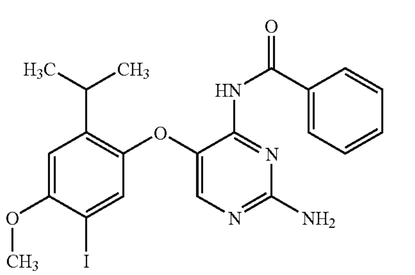 | N-[2-Amino-5-(5-iodo-2-isopropyl-4-methoxy-phenoxy)-pyrimidin-4-yl]-benzamide | 505 |

TABLE 1-continued

| # | Structure | Name (Autonom ™) | Mp (° C.) or M + H |
|---|---|---|---|
| 18 | 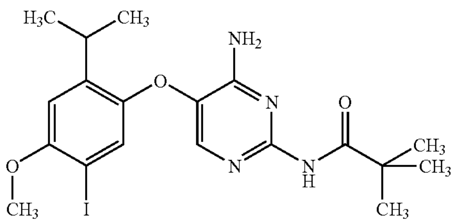 | N-[4-Amino-5-(5-iodo-2-isopropyl-4-methoxy-phenoxy)-pyrimidin-2-yl]-2,2-dimethyl-propionamide | 585 |
| 19 | 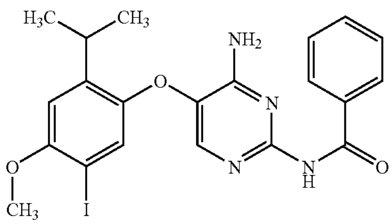 | N-[4-Amino-5-(5-iodo-2-isopropyl-4-methoxy-phenoxy)-pyrimidin-2-yl]-benzamide | 213.0-213.9° C. |
| 20 | 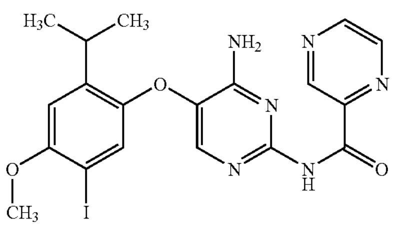 | Pyrazine-2-carboxylic acid [4-amino-5-(5-iodo-2-isopropyl-4-methoxy-phenoxy)-pyrimidin-2-yl]-amide | 221–223° C. |
| 21 | 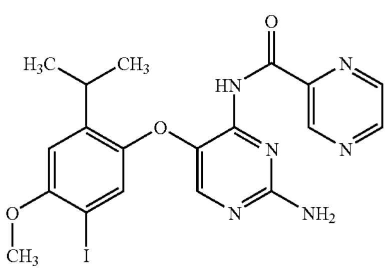 | Pyrazine-2-carboxylic acid [2-amino-5-(5-iodo-2-isopropyl-4-methoxy-phenoxy)-pyrimidin-4-yl]-amide | 232-234° C. |
| 22 | 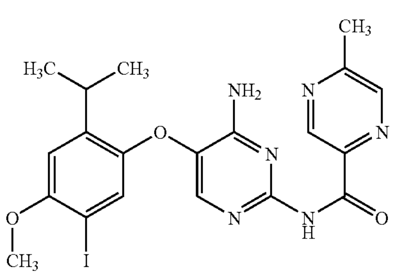 | 5-Methyl-pyrazine-2-carboxylic acid [4-amino-5-(5-iodo-2-isopropyl-4-methoxy-phenoxy)-pyrimidin-2-yl]-amide | 235-238° C. |
| 23 | 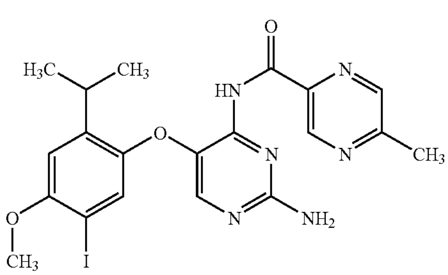 | 5-Methyl-pyrazine-2-carboxylic acid [2-amino-5-(5-iodo-2-isopropyl-4-methoxy-phenoxy)-pyrimidin-4-yl]-amide | 521 |

TABLE 1-continued

| # | Structure | Name (Autonom ™) | Mp (° C.) or M + H |
|---|---|---|---|
| 24 | 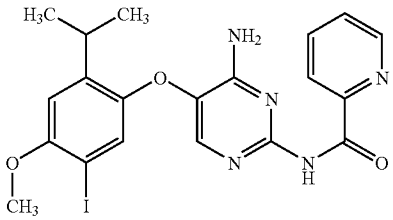 | Pyridine-2-carboxylic acid [4-amino-5-(5-iodo-2-isopropyl-4-methoxy-phenoxy)-pyrimidin-2-yl]-amide | 506 |
| 25 | 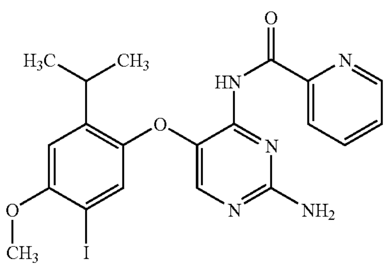 | Pyridine-2-carboxylic acid [2-amino-5-(5-iodo-2-isopropyl-4-methoxy-phenoxy)-pyrimidin-4-yl]-amide | 506 |
| 26 | 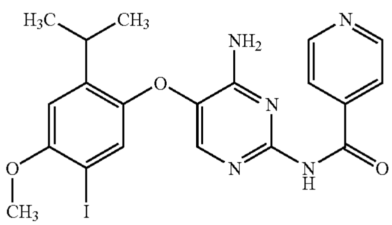 | N-[4-Amino-5-(5-iodo-2-isopropyl-4-methoxy-phenoxy)-pyrimidin-2-yl]-isonicotinamide | 506 |
| 27 | 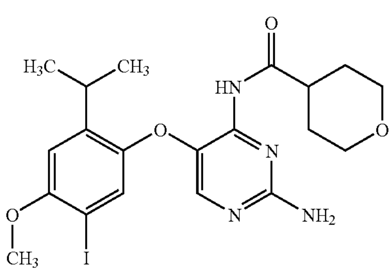 | Tetrahydro-pyran-4-carboxylic acid [2-amino-5-(5-iodo-2-isopropyl-4-methoxy-phenoxy)-pyrimidin-4-yl]-amide | 140-145° C. |
| 28 | 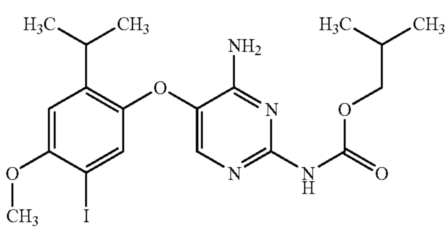 | [4-Amino-5-(5-iodo-2-isopropyl-4-methoxy-phenoxy)-pyrimidin-2-yl]-carbamic acid isobutyl ester | 205-207° C. |
| 29 | 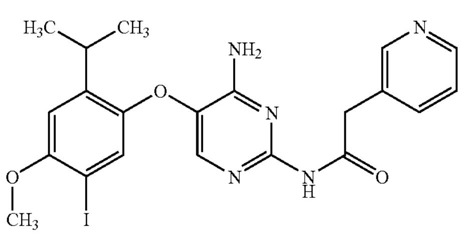 | N-[4-Amino-5-(5-iodo-2-isopropyl-4-methoxy-phenoxy)-pyrimidin-2-yl]-2-pyridin-3-yl-acetamide | 175.0-176.5° C. |

TABLE 1-continued

| # | Structure | Name (Autonom™) | Mp (° C.) or M + H |
|---|---|---|---|
| 30 | 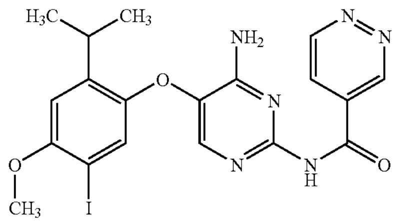 | Pyridazine-4-carboxylic acid [4-amino-5-(5-iodo-2-isopropyl-4-methoxy-phenoxy)-pyrimidin-2-yl]-amide | 204.9-206.6° C. |
| 31 | 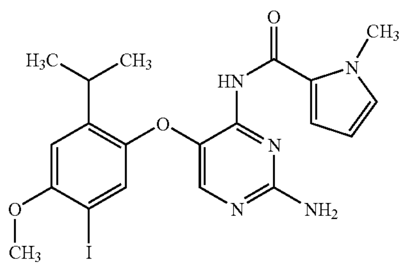 | 1-Methyl-1H-pyrrole-2-carboxylic acid [2-amino-5-(5-iodo-2-isopropyl-4-methoxy-phenoxy)-pyrimidin-4-yl]-amide | 508 |
| 32 | 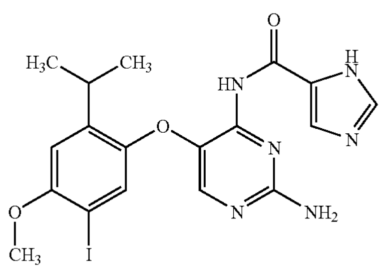 | 3H-Imidazole-4-carboxylic acid [2-amino-5-(5-iodo-2-isopropyl-4-methoxy-phenoxy)-pyrimidin-4-yl]-amide | 595 |
| 33 | 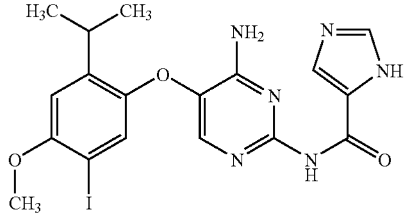 | 3H-Imidazole-4-carboxylic acid [4-amino-5-(5-iodo-2-isopropyl-4-methoxy-phenoxy)-pyrimidin-2-yl]-amide | 595 |
| 34 | 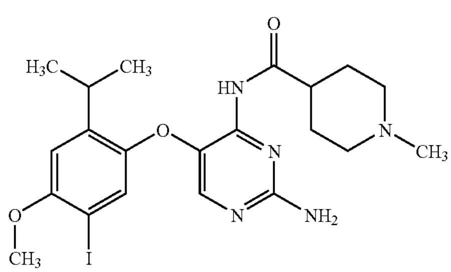 | 1-Methyl-piperidine-4-carboxylic acid [2-amino-5-(5-iodo-2-isopropyl-4-methoxy-phenoxy)-pyrimidin-4-yl]-amid | 526 |
| 35 | 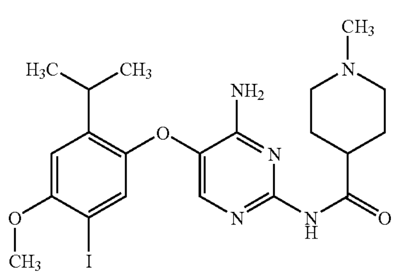 | 1-Methyl-piperidine-4-carboxylic acid [4-amino-5-(5-iodo-2-isopropyl-4-methoxy-phenoxy)-pyrimidin-2-yl]-amide | 526 |

TABLE 1-continued

| # | Structure | Name (Autonom™) | Mp (° C.) or M + H |
|---|---|---|---|
| 36 | 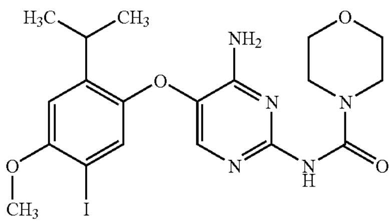 | Morpholine-4-carboxylic acid [4-amino-5-(5-iodo-2-isopropyl-4-methoxy-phenoxy)-pyrimidin-2-yl]-amide | 514 |
| 37 | 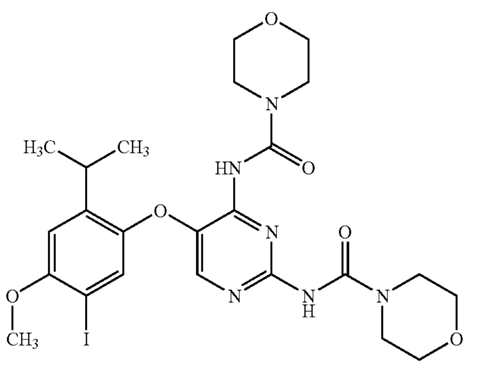 | Bis-morpholine-4-carboxylic acid [4-amino-5-(5-iodo-2-isopropyl-4-methoxy-phenoxy)-pyrimidin-2-yl]-amide | 627 |
| 38 | 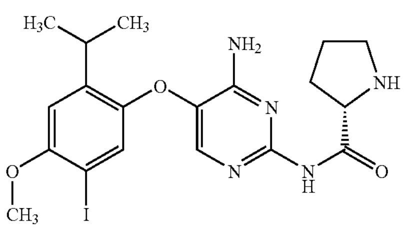 | Pyrrolidine-2-carboxylic acid [4-amino-5-(5-iodo-2-isopropyl-4-methoxy-phenoxy)-pyrimidin-2-yl]-amide | 498 |
| 39 | 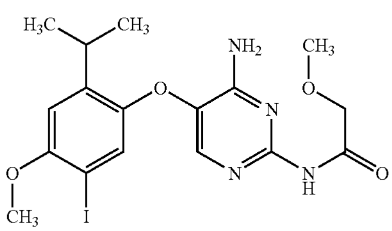 | N-[4-Amino-5-(5-iodo-2-isopropyl-4-methoxy-phenoxy)-pyrimidin-2-yl]-2-methoxy-acetamide | 155-156° C. |
| 40 | 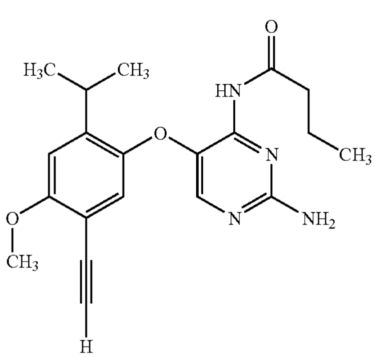 | N-[2-Amino-5-(5-ethynyl-2-isopropyl-4-methoxy-phenoxy)-pyrimidin-4-yl]-butyramide | 163.0-164.3° C. |

TABLE 1-continued

| # | Structure | Name (Autonom ™) | Mp (° C.) or M + H |
|---|---|---|---|
| 41 | 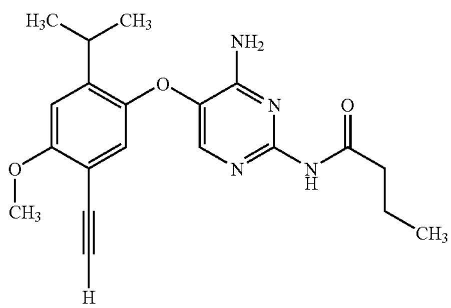 | N-[4-Amino-5-(5-ethynyl-2-isopropyl-4-methoxy-phenoxy)-pyrimidin-2-yl]-butyramide | 169.0-171.1° C. |
| 42 | 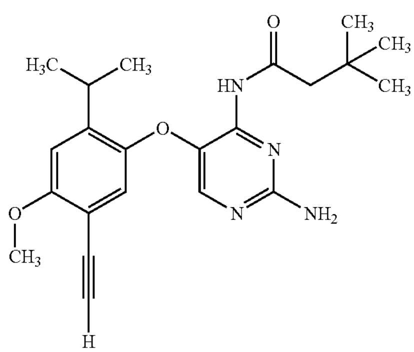 | N-[2-Amino-5-(5-ethynyl-2-isopropyl-4-methoxy-phenoxy)-pyrimidin-4-yl]-3,3-dimethyl-butyramide | 98.0-100.0° C. |
| 43 | 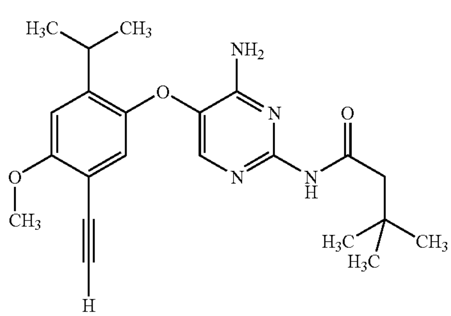 | N-[4-Amino-5-(5-ethynyl-2-isopropyl-4-methoxy-phenoxy)-pyrimidin-2-yl]-3,3-dimethyl-butyramide | 131.5-133.5° C. |
| 44 | 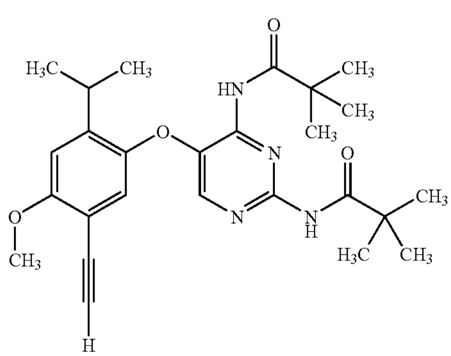 | N-[2-(2,2-Dimethyl-propionylamino)-5-(5-ethynyl-2-isopropyl-4-methoxy-phenoxy)-pyrimidin-4-yl]-2,2-dimethyl-propionamide | 100.1-103.7° C. |

TABLE 1-continued

| # | Structure | Name (Autonom ™) | Mp (° C.) or M + H |
|---|---|---|---|
| 45 | 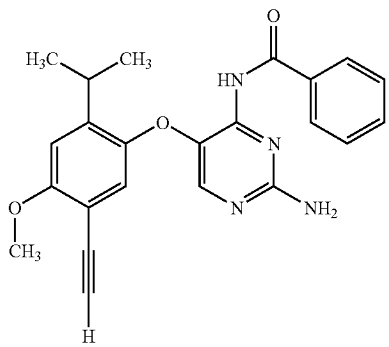 | N-[2-Amino-5-(5-ethynyl-2-isopropyl-4-methoxy-phenoxy)-pyrimidin-4-yl]-benzamide | 403 |
| 46 | 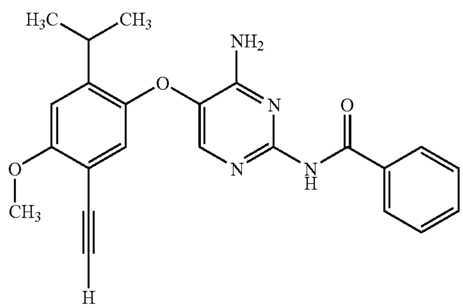 | N-[4-Amino-5-(5-ethynyl-2-isopropyl-4-methoxy-phenoxy)-pyrimidin-2-yl]-benzamide | 171.9-173.3° C. |
| 47 | 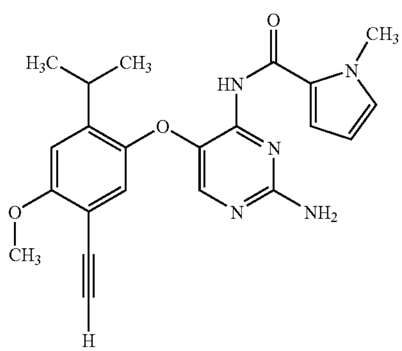 | 1-Methyl-1H-pyrrole-2-carboxylic acid [2-amino-5-(5-ethynyl-2-isopropyl-4-methoxy-phenoxy)-pyrimidin-4-yl]-amide | 72.2-82.3° C. |
| 48 | 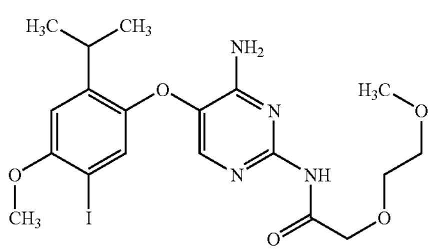 | N-[4-Amino-5-(5-iodo-2-isopropyl-4-methoxy-phenoxy)-pyrimidin-2-yl]-2-(2-methoxy-ethoxy)-acetamide | 144.0-145.9° C. |
| 49 | 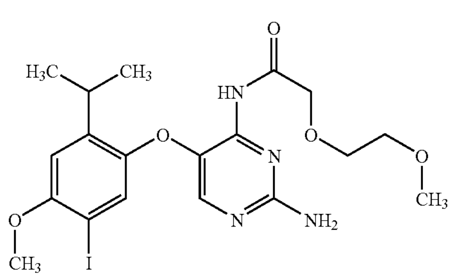 | N-[2-Amino-5-(5-iodo-2-isopropyl-4-methoxy-phenoxy)-pyrimidin-4-yl]-2-(2-methoxy-ethoxy)-acetamide | 173.0-174.3° C. |

TABLE 1-continued

| # | Structure | Name (Autonom ™) | Mp (° C.) or M + H |
|---|---|---|---|
| 50 | 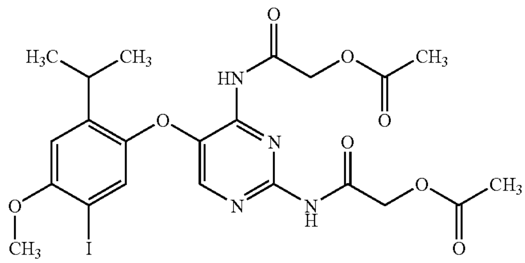 | Acetic acid [2-(2-acetoxy-acetylamino)-5-(5-iodo-2-isopropyl-4-methoxy-phenoxy)-pyrimidin-4-ylcarbamoyl]-methyl ester | 143-148° C. |
| 51 | 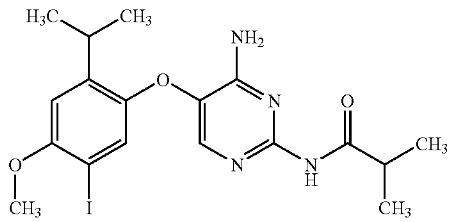 | N-[4-Amino-5-(5-iodo-2-isopropyl-4-methoxy-phenoxy)-pyrimidin-2-yl]-isobutyramide | 173.0-175.5° C. |
| 52 | 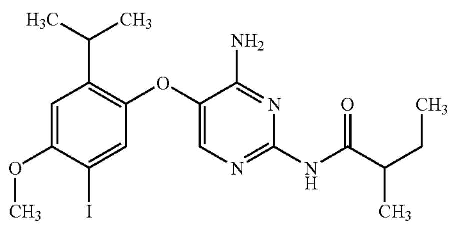 | N-[4-Amino-5-(5-iodo-2-isopropyl-4-methoxy-phenoxy)-pyrimidin-2-yl]-2-methyl-butyramide | 191.1-193.3° C. |
| 53 | 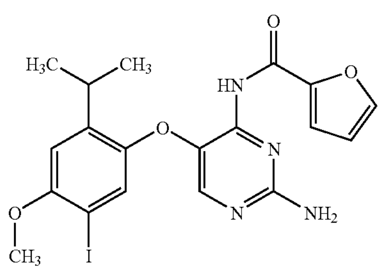 | Furan-2-carboxylic acid [2-amino-5-(5-iodo-2-isopropyl-4-methoxy-phenoxy)-pyrimidin-4-yl]-amide | 202-205° C. |
| 54 | 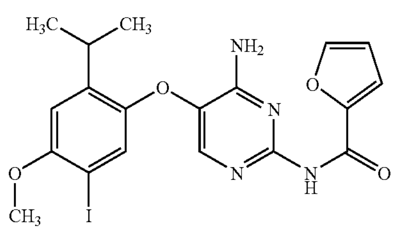 | Furan-2-carboxylic acid [4-amino-5-(5-iodo-2-isopropyl-4-methoxy-phenoxy)-pyrimidin-2-yl]-amide | 180-183° C. |
| 55 | 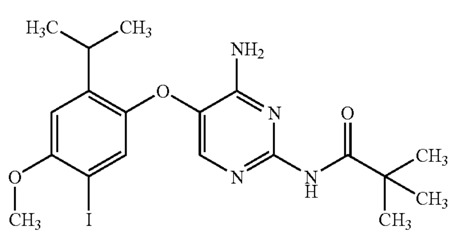 | N-[4-Amino-5-(5-iodo-2-isopropyl-4-methoxy-phenoxy)-pyrimidin-2-yl]-2,2-dimethyl-propionamide | 131.5-133.5° C. |

TABLE 1-continued

| # | Structure | Name (Autonom ™) | Mp (° C.) or M + H |
|---|---|---|---|
| 56 | 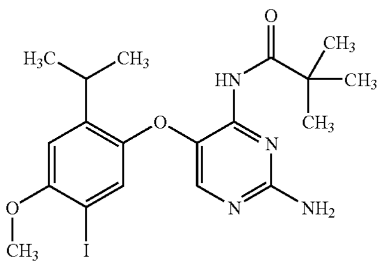 | N-[2-Amino-5-(5-iodo-2-isopropyl-4-methoxy-phenoxy)-pyrimidin-4-yl]-2,2-dimethyl-propionamide | 98.0-100.0° C. |
| 57 | 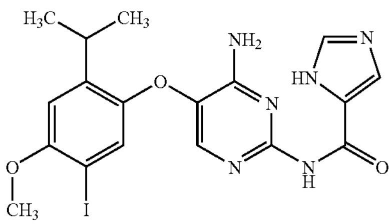 | 3H-Imidazole-4-carboxylic acid [4-amino-5-(5-iodo-2-isopropyl-4-methoxy-phenoxy)-pyrimidin-2-yl]-amide | 260-263° C. |
| 58 | 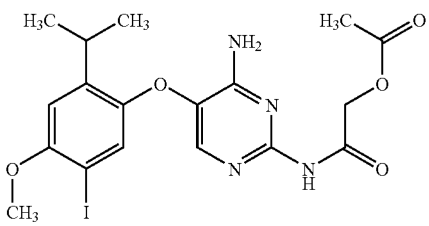 | Acetic acid [4-amino-5-(5-iodo-2-isopropyl-4-methoxy-phenoxy)-pyrimidin-2-ylcarbamoyl]-methyl ester | 209-210° C. |
| 59 | 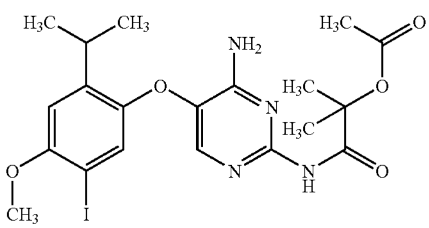 | Acetic acid 1-[4-amino-5-(5-iodo-2-isopropyl-4-methoxy-phenoxy)-pyrimidin-2-ylcarbamoyl]-1-methyl-ethyl ester | 158-160° C. |
| 60 | 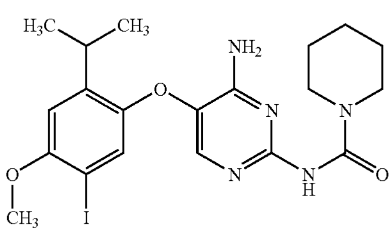 | Piperidine-1-carboxylic acid [4-amino-5-(5-iodo-2-isopropyl-4-methoxy-phenoxy)-pyrimidin-2-yl]-amide | 195.0-196.0° C. |
| 61 | 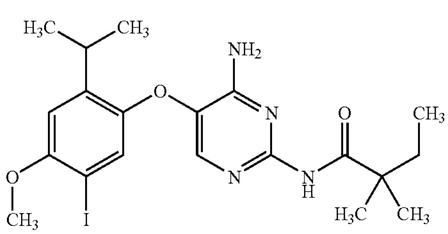 | N-[4-Amino-5-(5-iodo-2-isopropyl-4-methoxy-phenoxy)-pyrimidin-2-yl]-2,2-dimethyl-butyramide | 181.0-182.3° C. |

TABLE 1-continued

| # | Structure | Name (Autonom ™) | Mp (° C.) or M + H |
|---|---|---|---|
| 62 | 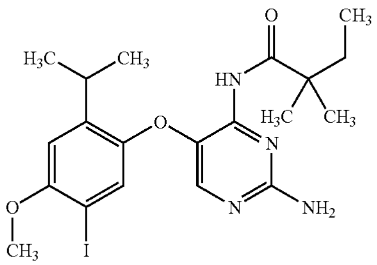 | N-[2-Amino-5-(5-iodo-2-isopropyl-4-methoxy-phenoxy)-pyrimidin-4-yl]-2,2-dimethyl-butyramide | 161.0-163.3° C. |
| 63 | 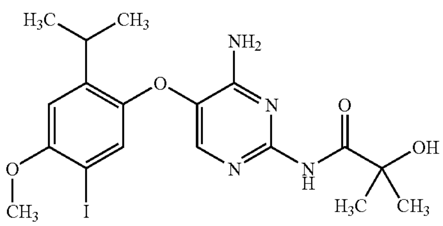 | N-[4-Amino-5-(5-iodo-2-isopropyl-4-methoxy-phenoxy)-pyrimidin-2-yl]-2-hydroxy-2-methyl-propionamide | 487 |
| 64 | 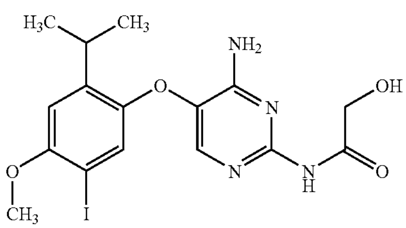 | N-[4-Amino-5-(5-iodo-2-isopropyl-4-methoxy-phenoxy)-pyrimidin-2-yl]-2-hydroxy-acetamide | 169-170° C. |
| 65 | 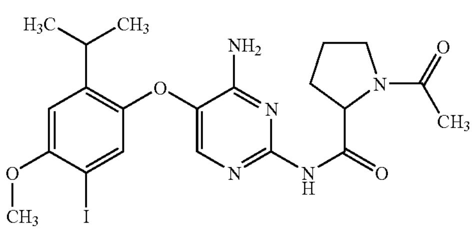 | 1-Acetyl-pyrrolidine-2-carboxylic acid [4-amino-5-(5-iodo-2-isopropyl-4-methoxy-phenoxy)-pyrimidin-2-yl]-amide | 150.0-152.5° C. |
| 66 | 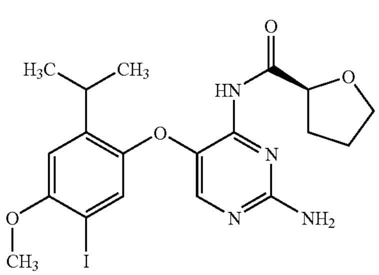 | Tetrahydro-furan-2-carboxylic acid [2-amino-5-(5-iodo-2-isopropyl-4-methoxy-phenoxy)-pyrimidin-4-yl]-amide | 220-222° C. |

TABLE 1-continued

| # | Structure | Name (Autonom ™) | Mp (° C.) or M + H |
|---|---|---|---|
| 67 | 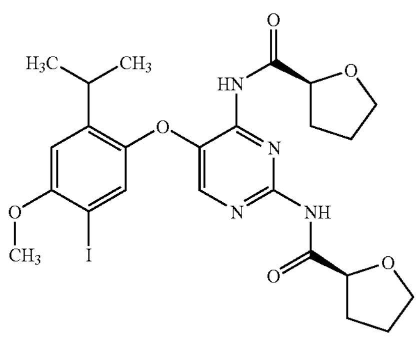 | Tetrahydro-furan-2-carboxylic acid [5-(5-iodo-2-isopropyl-4-methoxy-phenoxy)-2-(5-methoxy-pentanoylamino)-pyrimidin-4-yl]-amide | 146-147° C. |
| 68 | 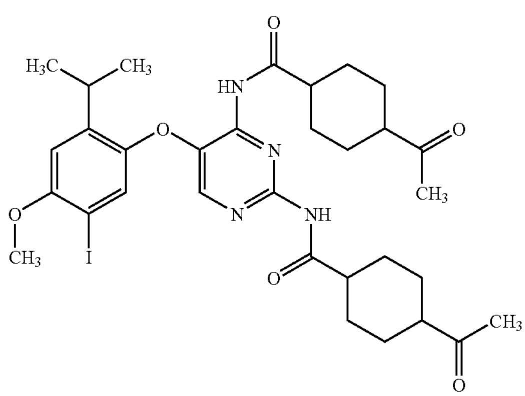 | 4-Acetyl-cyclohexanecarboxylic acid-[2-amino-5-(5-iodo-2-isopropyl-4-methoxy-phenoxy)-pyrimidin-4-yl]-amide | 191-192° C. |
| 69 | 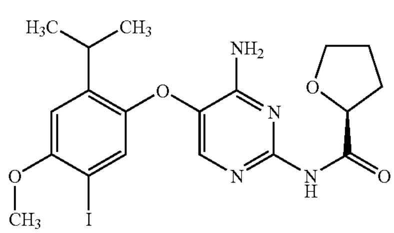 | Tetrahydro-furan-2-carboxylic acid [4-amino-5-(5-iodo-2-isopropyl-4-methoxy-phenoxy)-pyrimidin-2-yl]-amide | 499 |
| 70 | 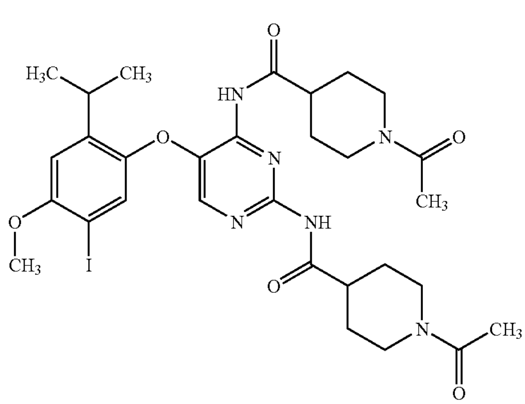 | Bis-1-Acetyl-piperidine-4-carboxylic acid [2-amino-5-(5-iodo-2-isopropyl-4-methoxy-phenoxy)-pyrimidin-4-yl]-amide | 146-150° C. |

TABLE 1-continued

| # | Structure | Name (Autonom ™) | Mp (° C.) or M + H |
|---|---|---|---|
| 71 | 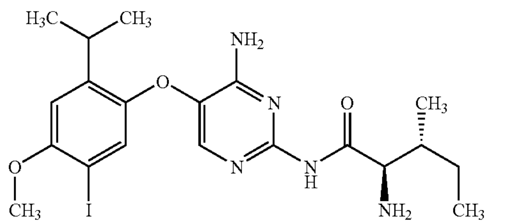 | 2-Amino-3-methyl-pentanoic acid [4-amino-5-(5-iodo-2-isopropyl-4-methoxy-phenoxy)-pyrimidin-2-yl]-amide | 116.0-118.3° C. |
| 72 | 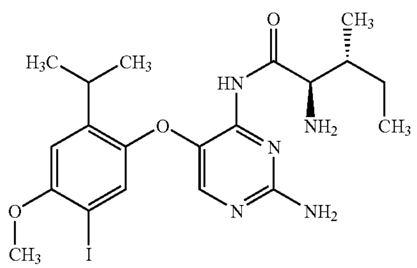 | 2-Amino-3-methyl-pentanoic acid [2-amino-5-(5-iodo-2-isopropyl-4-methoxy-phenoxy)-pyrimidin-4-yl]-amide | 97.8-101.9° C. |
| 73 | 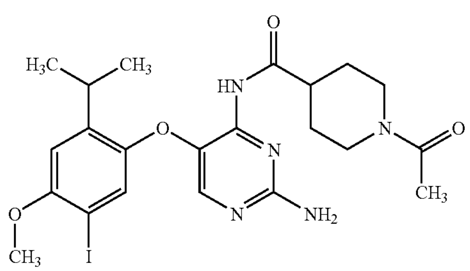 | 1-Acetyl-piperidine-4-carboxylic acid [2-amino-5-(5-iodo-2-isopropyl-4-methoxy-phenoxy)-pyrimidin-4-yl]-amide | 143-145° C. |
| 74 | 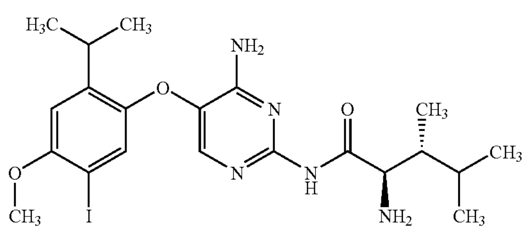 | 2-Amino-3,4-dimethyl-pentanoic acid [4-amino-5-(5-iodo-2-isopropyl-4-methoxy-phenoxy)-pyrimidin-2-yl]-amide | 101.9-106.9° C. |
| 75 | 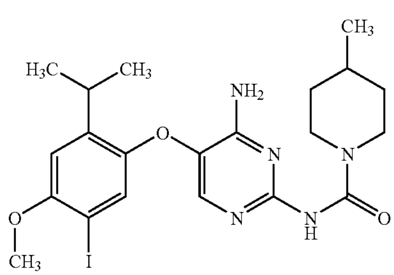 | 4-Methyl-piperidine-1-carboxylic acid [4-amino-5-(5-iodo-2-isopropyl-4-methoxy-phenoxy)-pyrimidin-2-yl]-amide | 526 |
| 76 | 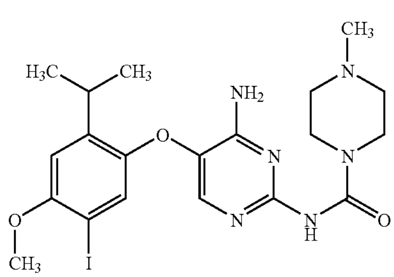 | 4-Methyl-piperazine-1-carboxylic acid [4-amino-5-(5-iodo-2-isopropyl-4-methoxy-phenoxy)-pyrimidin-2-yl]-amide | 527 |

TABLE 1-continued

| # | Structure | Name (Autonom ™) | Mp (° C.) or M + H |
|---|---|---|---|
| 77 | 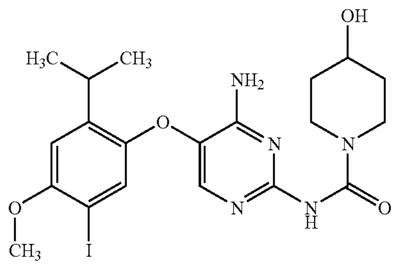 | 4-Hydroxy-piperidine-1-carboxylic acid [4-amino-5-(5-iodo-2-isopropyl-4-methoxy-phenoxy)-pyrimidin-2-yl]-amide | 178.2-180.0° C. |
| 78 | 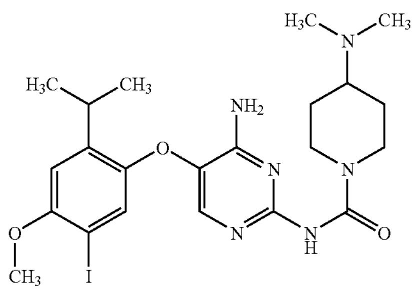 | 4-Dimethylamino-piperidine-1-carboxylic acid [4-amino-5-(5-iodo-2-isopropyl-4-methoxy-phenoxy)-pyrimidin-2-yl]-amide | 179.0-181.6° C. |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula (I) wherein L is a leaving group and $R^1$, $R^2$, $R^3$, $R^4$ and $R^d$ are as defined herein.

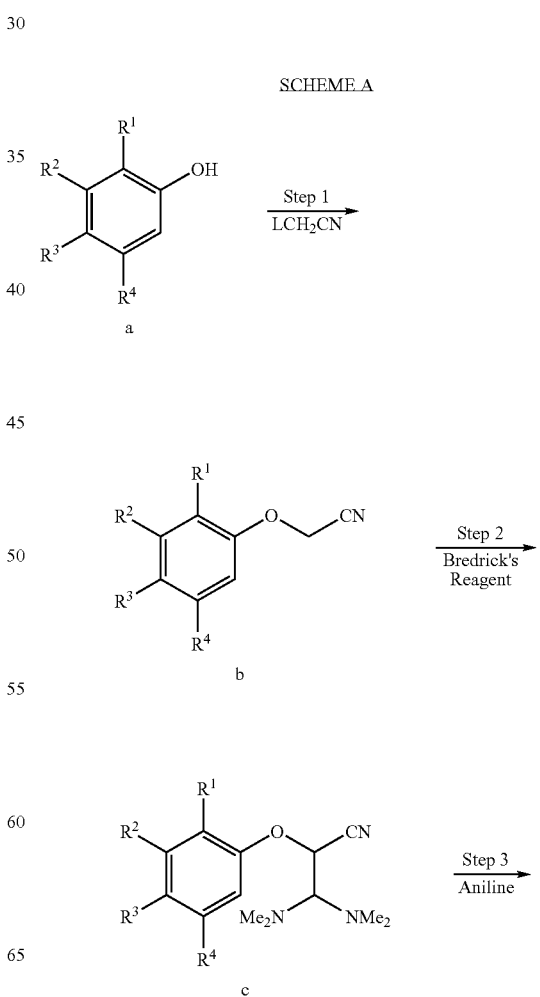

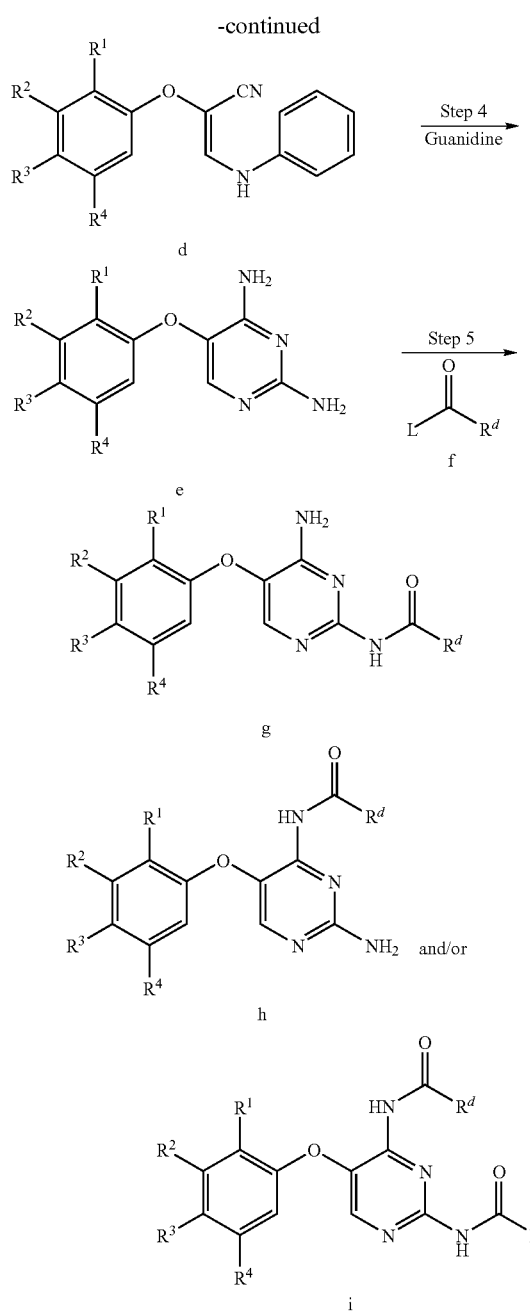

Where only a single equivalent of reagent f is used and $R^1$ is a bulky group such as isopropyl, compound g may be predominantly formed in step 5. Alternatively, diacyl compound i may be prepared by further acylation of monoacylated compound g or h. In certain embodiments compounds c and/or d need not be isolated as the reaction steps may be carried through in a single reaction vessel.

Scheme B below illustrates another synthetic procedure usable to prepare specific compounds of formula (I) wherein L is a leaving group and $R^1$, $R^2$, $R^3$ and $R^4$ are as defined herein.

SCHEME B

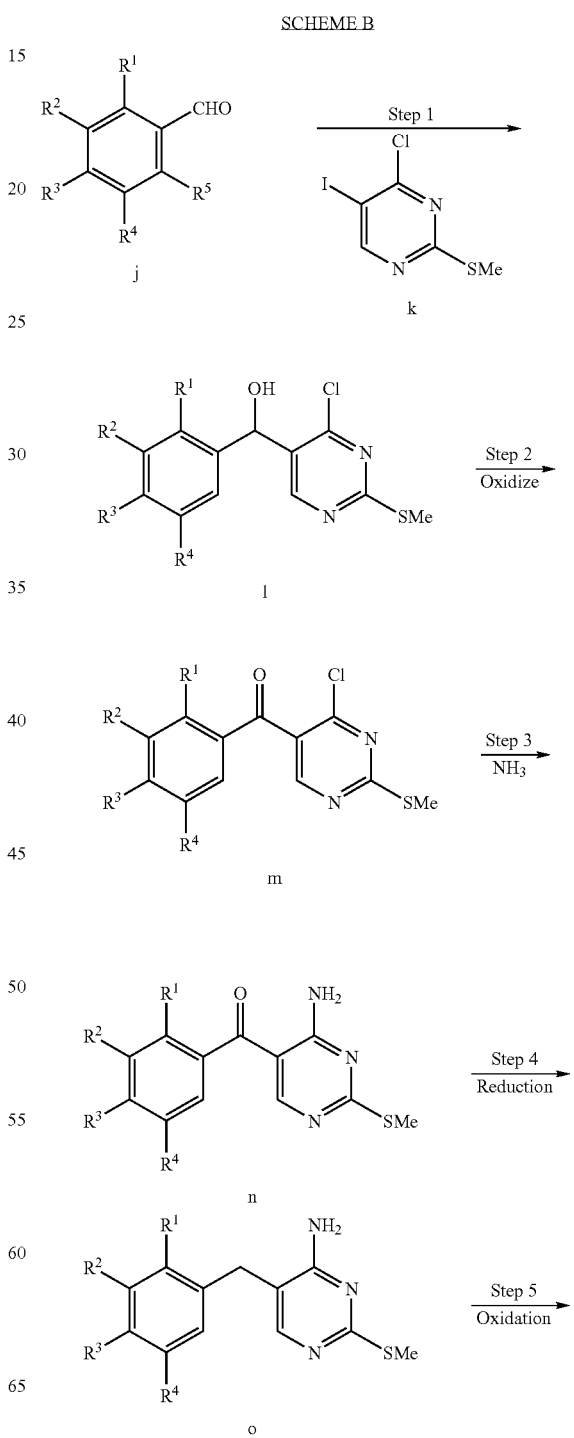

In step 1 of Scheme A, phenol a undergoes an O-alkylation by reaction with an acetonitrile reagent to form cyano ether compound b. Compound b is then treated with Bredrick's reagent (t-butoxybis(dimethylamino)methane) in step 2 to form bisdimethylamino compound c. In step 3 compound c is reacted with aniline to afford the aniline compound d. Compound d then undergoes reaction with guanidine in step 4 to provide phenoxy diamino pyrimidine e. Compound e, in step 5, is treated with acylating reagent f to afford diaminopyrimidine g, h and/or i, which are compounds of formula I in accordance with the invention. Reagent f may be, for example, an acid chloride or other acid halide, an anhydride, or like compound. Where two or more equivalents of reagent f are used in step 5, diacylated compound i may be formed.

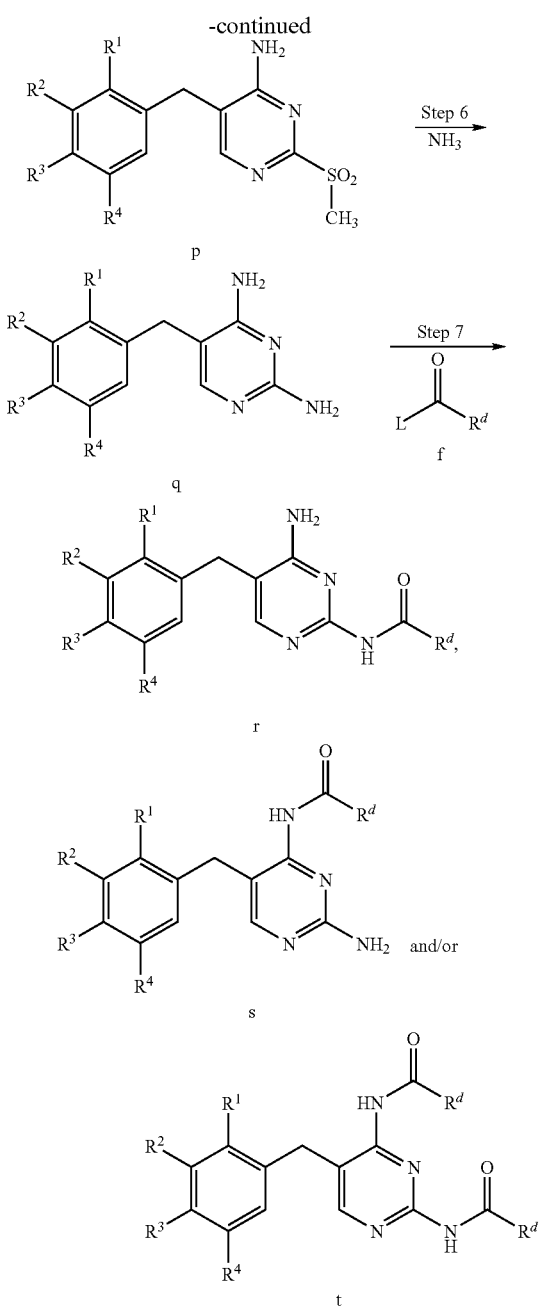

In Step 1 of Scheme B, benzaldehyde i is alkylated with the Grignard reagent derived from 4-chloro-5-iodo-2-methylsulfanyl-pyrimidine k or like iodopyrimidine to provide an alpha-hydroxy benzyl pyrimidine l. The iodopyrimidine used in this step may be prepared according to the procedure described by T. Sakamoto, et al., Chem. Pharm. Bull., 34 1986, p. 2719. Numerous substituted benzaldehydes a are commercially available or are readily prepared by techniques well known to those skilled in the art. In many instances, a "masked aldehyde", such as an imine or oxazoline, may be used to allow introduction of desired functionalities to benzaldehyde i, after which the masked aldehyde is deprotected to provide the free aldehyde group.

In step 2, alpha-hydroxy benzyl pyrimidine l is oxidized to provide ketone compound m. In step 3, a first amination by reaction of ammonia with ketone compound m yields aminopyrimidine phenone compound n. In step 4 the carbonyl group of compound n is reduced to a methylene group to provide benzyl aminopyridine compound o. In step 5, an oxidation of the sulfur on compound o yields methanesulfonyl compound p. A second amination occurs in step 6 in which amino methanesulfonyl benzylpyrimidine p is treated with ammonia to displace the methanesulfonyl group and provide diamino benzylpyrimidine q. The diamino benzylpyrimidine q is then subject to acylation in step 7 to afford mono and/or di-acylated compounds r, s and/or t. As noted above, use of two or more equivalents of reagent f in step 5 may provide diacylated compound s. while only a single equivalent of reagent f in the presence of a bulky R$^1$ group may provide predominantly monoacylated compound r.

Numerous variations on the above procedure are possible and will suggest themselves to those skilled in the art upon review of this disclosure. Specific details for producing compounds of the invention are described in the Examples section below.

Utility

The compounds of the invention are usable as prodrugs for the treatment of a wide range of genitorurinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatitis, pelvic pain syndrome, prostatodynia, cystitis, and idiopathic bladder hypersensitivity, and other symptoms related to overactive bladder.

The compounds of the invention are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

Additionally, compounds of the invention are useful for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease. The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

Abbreviations

DCM dichloromethane
DMF N,N-dimethylformamide
DMAP 4-dimethylaminopyridine
EtOAc ethyl acetate
EtOH ethanol
gc gas chromatography
HMPA hexamethylphosphoramide
hplc high performance liquid chromatography
mCPBA m-chloroperbenzoic acid
MeCN acetonitrile
NMP N-methylpyrrolidinone
TEA triethylamine
THF tetrahydrofuran
LDA lithium diisopropylamine
TLC thin layer chromatography Example 1

N-[4-Amino-5-(5-iodo-2-isopropyl-4-methoxy-phenoxy)-pyrimidin-2-yl]-isobutyramide and N-[5-(5-Iodo-2-isopropyl-4-methoxy-phenoxy)-4-isobutylamino-pyrimidin-2-yl]-isobutyramide The synthetic procedure used in this Example is outlined in Scheme C.

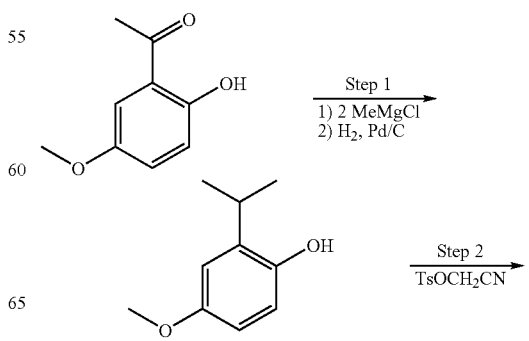

-continued

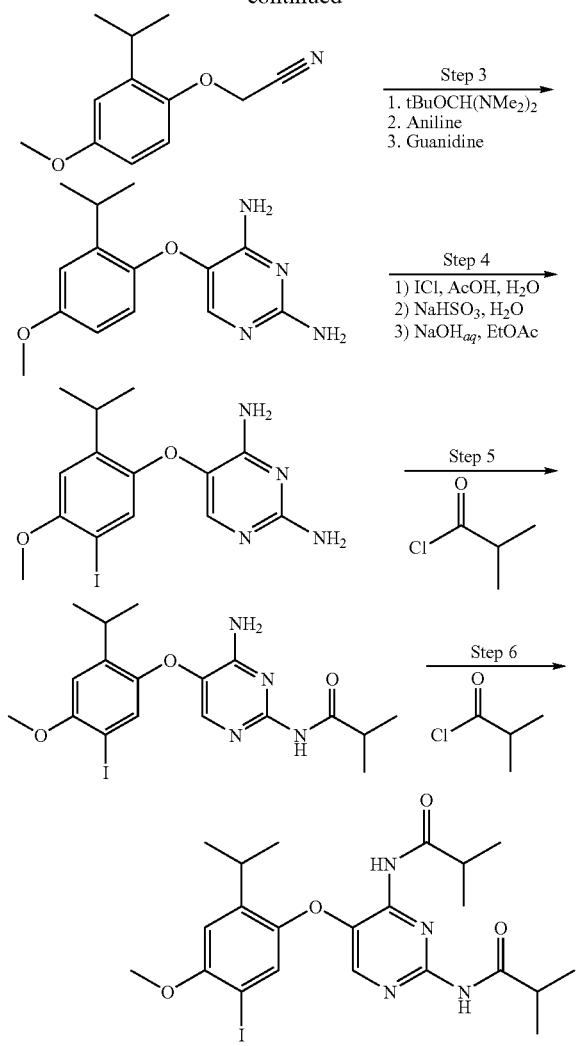

Step 1 2-Isopropyl-4-methoxy-phenol

To a cooled solution of 1-(2-Hydroxy-5-methoxy-phenyl)-ethanone (10.0 g) in 80 mL of THF was gradually added 46.4 g of 3M solution of MeMgCl in THF at a rate such that the reaction mixture temperature did not exceed 25 degrees C. Following addition of the MeMgCl solution, the reaction mixture was stirred at ambient temperature for 18 hours. To the stirred solution was then added 10% palladium on carbon (1.02 g, 50% water wet) suspended in 4 mL of THF. The reaction mixture was placed under a hydrogen atmosphere at 5 psig and cooling was applied to maintain a temperature of approximately 25° C. To the cooled mixture was gradually added concentrated HCl (20 mL) while maintaining the reaction temperature at 25° C. The resultant mixture was stirred at ambient temperature for 18 hours, then treated with 45 mL water and filtered through a bed of Celite to remove suspended catalyst. The filter cake was rinsed with EtOAc and the combined filtrate was separated. The organic phase was washed with water, then concentrated under reduced pressure to give 10.4 g of 2-isopropyl-4-methoxy-phenol, MS (M+H)= 167. This product was dissolved in 2-butanone (20.4 g) and the crude solution was employed directly in the next step.

Step 2
(2-Isopropyl-4-methoxy-phenoxy)-acetonitrile

A stirred slurry of toluene-4-sulfonic acid cyanomethyl ester (13.0 g), potassium carbonate (13.0 g) and 2-isopropyl-4-methoxyphenol (9.57 g) in 85 mL of 2-butanone was heated to 55-60 degrees C. for 4 days, then heated to reflux for 18 hours. The resultant slurry was cooled and filtered to remove solids. The filtrate was concentrated under reduced pressure and the residue was redissolved in toluene. The toluene solution was extracted with 1N KOH, and the organic phase was concentrated under reduced pressure to give 20.6 g of a 1:1 (by weight) solution of (2-Isopropyl-4-methoxy-phenoxy)-acetonitrile in toluene, which was used directly in the next step. A anliquot (0.967 g) of this solution was concentrated to dryness to give 0.509 g of crude (2-Isopropyl-4-methoxy-phenoxy)-acetonitrile, MS (M+H)=206.

Step 3 5-(2-Isopropyl-4-methoxy-phenoxy)-pyrimidine-2,4-diamine

A 1:1 (by weight) solution of toluene and (2-Isopropyl-4-methoxy-phenoxy)-acetonitrile (10.6 g of the nitrile compound) was concentrated under reduced pressure and the residue was treated with 10.8 g of tert-butoxybis(dimethyl amino)methane (Bredrick's Reagent). The resulting mixture was dissolved in 22 mL of DMF and the solution was heated to 110 degrees C. for 2 hours. The DMF solution was cooled and transferred onto 14.7 g of aniline hydrochloride. The resulting mixture was heated to 120 degrees C. for 22 hours, then cooled, diluted with 25 mL toluene, then with 70 mL of water. The organic layer was separated, washed with water, and concentrated under reduced pressure. The residue was transferred into 25 mL DMF, and the DMF solution was transferred onto 6.01 g of guanidine carbonate. The resulting mixture was heated to 120 degrees C. for 3 days, then cooled, diluted with 10 mL of EtOAc, then reheated to 60 degrees C. Water (75.1 mL) was added and the resultant mixture was allowed to cool to ambient temperature. The precipitated solid was collected by filtration, rinsed with isopropanol and dried under vacuum at 50 degrees to give 9.62 g of 5-(2-isopropyl-4-methoxy-phenoxy)-pyrimidine-2,4-diamine, m.p. 170-171 degrees C., MS (M+H)=275.

Step 4 5-(5-Iodo-2-isopropyl-4-methoxy-phenoxy)-pyrimidine-2,4-diamine

To a solution of 5-(2-isopropyl-4-methoxy-phenoxy)-pyrimidine-2,4-diamine (6.50 g) in mL glacial Acetic acid was added a solution of 9.205 g ICl (iodine monochloride) in 8 mL of acetic acid, with addition carried out at a rate such that the temperature of the resulting mixture did not exceed 24 degrees C. Water (11.0 mL) was added and the resultant mixture was stirred at 25 degrees C. for 42 hours. Excess ICl was decomposed by the addition of aqueous solution of sodium bisulfite (3.5 mL) at a rate such that the temperature of the reaction mixture did not exceed 20 degrees C. Water (40 mL) was added, and the precipitate was collected by filtration and air-dried to give 8.86 g of crude 5-(5-iodo-2-isopropyl-4-methoxy-phenoxy)-pyrimidine-2,4-diamine. A suspension of the crude product in 90 mL water was made basic by addition of 50% NaOH, and the resulting solution was extracted into warm EtOAc. The combined organic layers were filtered and EtOAc was replaced by isopropanol via distillation. To the hot isopropanol solution was added 3.4 mL of 6N HCl and the resultant mixture was cooled slowly to 15 degrees C. Crystals of the resulting HCl salt were isolated by filtration, rinsed with isopropanol, and dried under vacuum at 70 degrees C. to give 6.08 g (58.8%) of 5-(5-iodo-2-isopropyl-4-methoxy-phenoxy)-pyrimidine-2,4-diamine hydrochloride salt, m.p.=262.0-263.0° C., MS (M+H)=401.

Step 5 N-[4-Amino-5-(5-iodo-2-isopropyl-4-methoxy-phenoxy)-pyrimidin-2-yl]-isobutyramide To 5-(5-iodo-2-isopropyl-4-methoxy-phenoxy)-pyrimidine-2,4-diamine (1 g, 2.50 mmol), dissolved in anhydrous tetrahydrofuran, was added triethylamine (0.38 mL, 2.75 mmol) and isobutyryl chloride (0.29 mL, 2.75 mmol). After stirring 30 minutes, the reaction was concentrated under reduced pressure. The residue was dissolved in dichloromethane (100 mL), and the dichloromethane layer was washed with water, dried using anhydrous sodium sulfate, and concentrated under reduced pressure. Purification by silica gel column chromatography eluting with 96/4/0.1 dichloromethane/methanol/ammonium hydroxide yielded 634 mg (54%) of N-[4-amino-5-(5-iodo-2-isopropyl-4-methoxy-phenoxy)-pyrimidin-2-yl]-isobutyramide as pale yellow solid, MS (M+H)=471.

Step 6 N-[5-(5-Iodo-2-isopropyl-4-methoxy-phenoxy)-4-isobutyrylamino-pyrimidin-2-yl]-isobutyramide To N-[4-amino-5-(5-iodo-2-isopropyl-4-methoxy-phenoxy)-pyrimidin-2-yl]-isobutyramide (386 mg, 0.82 mmol), dissolved in anhydrous tetrahydrofuran, was added triethylamine (0.13 mL, 0.90 mmol) and isobutyryl chloride (0.09 mL, 0.90 mmol). After stirring one hour, the reaction was concentrated under reduced pressure. The concentrate was dissolved in dichloromethane (50 mL), and the dichloromethane layer was washed with water, dried using anhydrous sodium sulfate, and concentrated under reduced pressure. Purification by preparatory TLC plates (98/2/0.5 dichloromethane/methanol/ammonium hydroxide) yielded 96 mg (22%) of N-[5-(5-iodo-2-isopropyl-4-methoxy-phenoxy)-4-isobutyrylamino-pyrimidin-2-yl]-isobutyramide as white solid, MS (M+H)=541.

Example 2

N-[4-Amino-5-(5-iodo-2-isopropyl-4-methoxy-phenoxy)-pyrimidin-2-yl]-butyramide and N-[2-Butyrylamino-5-(5-iodo-2-isopropyl-4-methoxy-phenoxy)-pyrimidin-4-yl]-butyramide

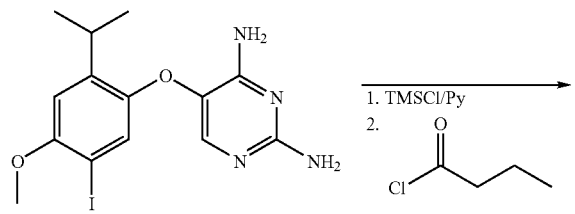

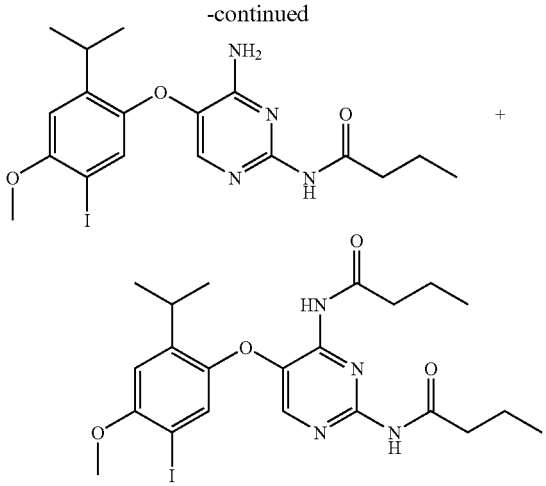

To a solution of 5-(5-iodo-2-isopropyl-4-methoxy-phenoxy)-pyrimidine-2,4-diamine (1.0 g, 2.5 mmoles) in dichloromethane (80 ml) and pyridine (5 ml) at 0° C. was added chlorotrimethyl silane (3.2 ml, 25.2 mmoles). The mixture was stirred at room temperature for 2.5 hours, then cooled to at 0° C. and butyryl chloride (0.54 ml, 5.2 mmoles) was added. The reaction was stirred at 0° C. for 2.5 hours, and then methanol (20 ml) was added. The reaction was stirred at room temperature for 60 hours. The reaction mixture was concentrated under reduced pressure, and the residue was partitioned between dichloromethane and water. The organic phase was separated and washed with brine, dried over anhydrous sodium sulfate, filtered, and concentrated under reduced pressure. The residue was purified by silica gel chromatography (0.5%, 1% methanol in dichloromethane with 0.1% concentrated ammonium hydroxide aqueous solution) to give crude N-[4-amino-5-(5-iodo-2-isopropyl-4-methoxy-phenoxy)-pyrimidin-2-yl]-butyramide and N-[2-butyrylamino-5-(5-iodo-2-isopropyl-4-methoxy-phenoxy)-pyrimidin-4-yl]-butyramide, which were loaded on preparative TLC plates separately, eluted with 5% methanol in dichloromethane to give pure N-[2-butyrylamino-5-(5-iodo-2-isopropyl-4-methoxy-phenoxy)-pyrimidin-4-yl]-butyramide (145 mgs), M+1: 541, and pure N-[4-amino-5-(5-iodo-2-isopropyl-4-methoxy-phenoxy)-pyrimidin-2-yl]-butyramide (425 mgs), MS (M+H)=471.

Example 3

Pentanoic acid [4-amino-5-(5-iodo-2-isopropyl-4-methoxy-phenoxy)-pyrimidin-2-yl]-amide and Pentanoic acid [5-(5-iodo-2-isopropyl-4-methoxy-phenoxy)-2-pentanoylamino-pyrimidin-4-yl]-amide

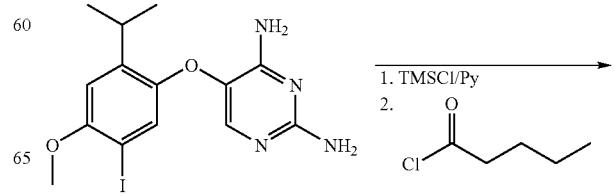

-continued

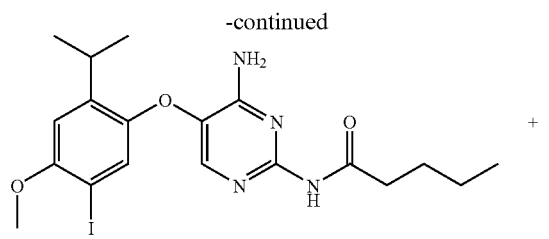

Example 4

N-[4-Amino-5-(5-iodo-2-isopropyl-4-methoxy-phenoxy)-pyrimidin-2-yl]-succinamic acid

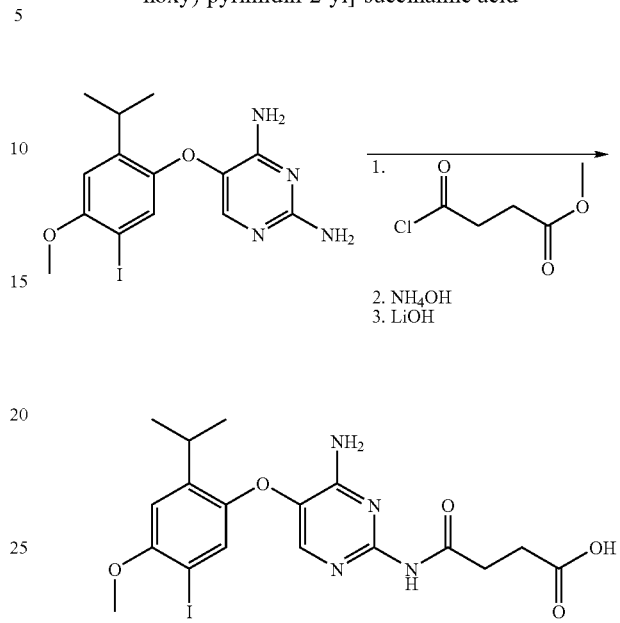

To a 0° C. solution of 5-(5-iodo-2-isopropyl-4-methoxy-phenoxy)-pyrimidine-2,4-diamine (1.0 g, 2.5 mmoles) in dichloromethane (80 ml) and pyridine (3 ml), was slowly added valeryl chloride (2.4 ml, 20.2 mmoles). The mixture was stirred at room temperature for 60 hours, and then solvent was removed under reduced pressure. The residue was washed twice with water and then dissolved in dichloromethane. This organic phase was dried over anhydrous sodium sulfate, filtered, and concentrated under reduced pressure. The residue was passed through a silica gel plug (40% ethyl acetate in hexane). The crude mixture was dissolved in a mixture of concentrated ammonium hydroxide aqueous solution and methanol (3 ml/27 ml) and stirred at room temperature for 15 minutes. Solvent was removed under reduced pressure, and the residue was purified by silica gel chromatography (20%, 35% ethyl acetate in hexane), to give crude pentanoic acid [5-(5-iodo-2-isopropyl-4-methoxy-phenoxy)-2-pentanoylamino-pyrimidin-4-yl]-amide was obtained, which was crystallized from ether and hexane to give pure pentanoic acid [5-(5-iodo-2-isopropyl-4-methoxy-phenoxy)-2-pentanoylamino-pyrimidin-4-yl]-amide (141 mg) as white solid, MS (M+H)=569. The filtrate from the recrystallization was dried and re-dissolved in a mixture of concentrated ammonium hydroxide aqueous solution and methanol (10 ml/40 ml) and stirred at room temperature for 5 hours. This solution was concentrated under reduced pressure, and the residue was partitioned between dichloromethane and water. The organic phase was washed with brine, dried over anhydrous sodium sulfate, filtered, and concentrated under reduced pressure. The residue was purified by silica gel chromatography (30% ethyl acetate in hexanes), and recrystallized from ethyl acetate and hexane to give pure pentanoic acid [4-amino-5-(5-iodo-2-isopropyl-4-methoxy-phenoxy)-pyrimidin-2-yl]-amide (395 mg) as white solid, MS (M+H)=485.

To a solution of 5-(5-iodo-2-isopropyl-4-methoxy-phenoxy)-pyrimidine-2,4-diamine (0.56 g, 1.4 mmoles) in dichloromethane (40 ml) and pyridine (4 ml) was slowly added methyl 4-chloro-4-oxobutyrate (1.3 ml, 7.5 mmoles). The mixture was stirred at room temperature for 60 hours, and then solvent was removed under reduced pressure. The residue was washed twice with water, dissolved in a mixture of concentrated aqueous ammonium hydroxide and methanol (10 ml/40 ml), and stirred at room temperature for one hour. Solvent was evaporated under reduced pressure and the residue was partitioned between dichloromethane and water. The organic phase was washed with brine, dried over anhydrous sodium sulfate, filtered and concentrated under reduced pressure. The residue was purified by silica gel chromatography (1% methanol in dichloromethane) to give crude N-[4-amino-5-(5-iodo-2-isopropyl-4-methoxy-phenoxy)-pyrimidin-2-yl]-succinamic acid methyl ester (0.54 g, not shown) as a foam, MS (M+H)=515.

To a solution of N-[4-amino-5-(5-iodo-2-isopropyl-4-methoxy-phenoxy)-pyrimidin-2-yl]-succinamic acid methyl ester (0.54 g, 1.05 mmoles) in THF (20 ml) was added a solution of Lithium hydroxide (0.33 g, 13.8 mmoles) in water (10 ml). The mixture was stirred at room temperature for 4 hours, then concentrated under reduced pressure. The aqueous residue was pH adjusted to pH=8, washed with EtOAc, and lyophilized for 36 hours. The resulting solid was washed with 30% methanol in ethyl acetate, and filtered. The filtrate was evaporated and the residue was washed twice with dichloromethane, dissolved in water and pH adjusted pH=7 by addition of 0.5 N HCl aqueous solution. The resulting precipitate was recrystallized from water, and the crystals were washed with dichloromethane/ether to give 40 mg of N-[4-Amino-5-(5-iodo-2-isopropyl-4-methoxy-phenoxy)-pyrimidin-2-yl]-succinamic acid as a light yellow solid. MS (M+H)=501.

Example 5

2-Amino-N-[4-amino-5-(5-iodo-2-isopropyl-4-methoxy-phenoxy)-pyrimidin-2-yl]-3-methyl-butyramide

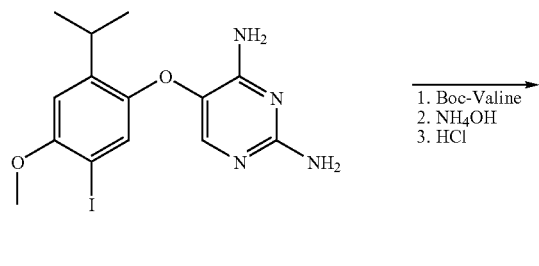

To a suspension of compound 5-(5-iodo-2-isopropyl-4-methoxy-phenoxy)-pyrimidine-2,4-diamine (1.0 g, 2.5 mmoles), Boc-DL-valine (1.22 g, 5.6 mmoles), and 4-dimethylaminopyridine (1.0 g, 8.2 mmoles) in dichloromethane, was added 1,3-dicyclohexylcarbodiimide (2.4 g, 11.6 mmoles). The mixture was stirred at room temperature for 60 hours, and solids were filtered off. The filtrate was evaporated and the residue was dissolved in a mixture of concentrated aqueous ammonium hydroxide and methanol (5 ml/45 ml) and stirred at room temperature for 5 hours. Solvent was evaporated under reduced pressure and the residue was partitioned between dichloromethane and 0.5 N aqueous HCl. The organic phase was washed with brine, dried over anhydrous sodium sulfate, filtered and concentrated under reduced pressure. The residue was purified by silica gel chromatography (30% ethyl acetate in hexane) to give Boc-protected 2-Amino-N-[4-amino-5-(5-iodo-2-isopropyl-4-methoxy-phenoxy)-pyrimidin-2-yl]-3-methyl-butyramide as a white foam (0.2 g), MS (M+H)=600. This Boc compound was dissolved in dichloromethane (3 ml) and 1M HCl in diethyl ether (10 ml) was added. The mixture was stirred for 4 hours at room temperature, and 10 ml of additional diethyl ether was added. The resulting solid precipitate was collected and crystallized from isopropanol and ether to give 2-amino-N-[4-amino-5-(5-iodo-2-isopropyl-4-methoxy-phenoxy)-pyrimidin-2-yl]-3-methyl-butyramide as white solid (0.12 g), MS (M+H)=500.

Example 6

N-[4-Amino-5-(5-iodo-2-isopropyl-4-methoxy-phenoxy)-pyrimidin-2-yl]-acetamide and N-[2-Acetylamino-5-(5-iodo-2-isopropyl-4-methoxy-phenoxy)-pyrimidin-4-yl]-acetamide

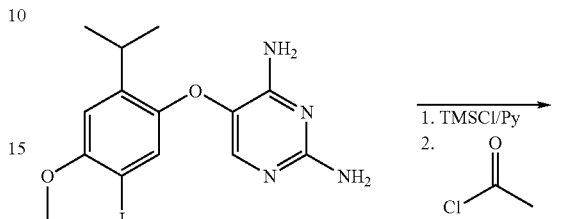

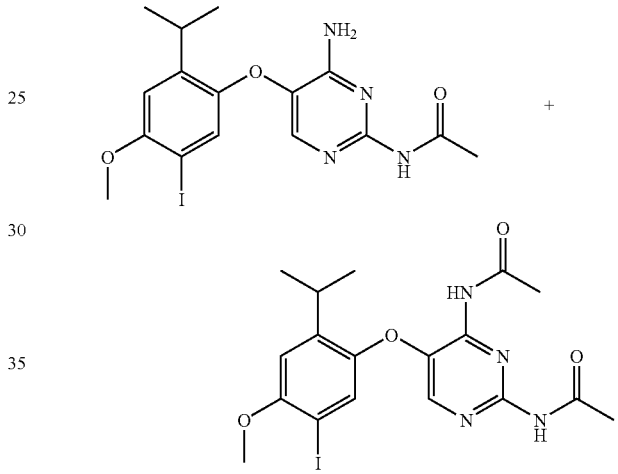

To a solution of 5-(5-iodo-2-isopropyl-4-methoxy-phenoxy)-pyrimidine-2,4-diamine (1.0 g, 2.5 mmoles) in $CH_2Cl_2$ (80 ml) cooled at 0° C. was added pyridine (2.6 g, 36 mmole) and trimethylsilylchloride (2.70 g, 25 mmole). The reaction mixture was stirred at room temperature for two hours, then recooled to 0° C. and acetyl chloride (0.22 g, 2.75 mmole) was added dropwise. After stirring at 0° C. for 90 minutes, methanol (20 ml) was added and stirring was continued for 16 hours. Solvent was removed under reduced pressure and the residue was treated with water (400 ml). The white insoluble material was collected by filtration and subject to flash chromatography on silica gel, eluting with 2% $CH_3OH$, 0.1% $NH_4OH$ in $CH_2Cl_2$ to give N-[4-amino-5-(5-iodo-2-isopropyl-4-methoxy-phenoxy)-pyrimidin-2-yl]-acetamide (0.094 g, MS (M+H)=443), N-[2-Acetylamino-5-(5-iodo-2-isopropyl-4-methoxy-phenoxy)-pyrimidin-4-yl]-acetamide (0.187 g, MS (M+H)=485), and a third fraction containing a mixture of N-[4-amino-5-(5-iodo-2-isopropyl-4-methoxy-phenoxy)-pyrimidin-2-yl]-acetamide and N-[2-Acetylamino-5-(5-iodo-2-isopropyl-4-methoxy-phenoxy)-pyrimidin-4-yl]-acetamide (0.524 g).

Similarly prepared were [4-Amino-5-(5-iodo-2-isopropyl-4-methoxy-phenoxy)-pyrimidin-2-yl]-carbamic acid ethyl ester (MS (M+H)=473) and [4-Ethoxycarbonylamino-5-(5- iodo-2-isopropyl-4-methoxy-phenoxy)-pyrimidin-2-yl]-carbamic acid ethyl ester (MS (M+H)=545).

Example 7

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | Grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 8

$P2X_3/P2X_{2/3}$ FLIPR (Fluorometric Imaging Plate Reader) Assay

CHO-K1 cells were transfected with cloned rat $P2X_3$ or human $P2X_{2/3}$ receptor subunits and passaged in flasks. 18-24 hours before the FLIPR experiment, cells were released from their flasks, centrifuged, and resuspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 µl/well agonist or vehicle addition. The agonist was a 2× solution of α,β-meATP producing a final concentration of 1 µM ($P2X_3$) or 5 µM ($P2X_{2/3}$). Fluorescence was measured for an additional 2 minutes at 1 second intervals after agonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the $P2X_3$ receptor. The compound N-[4-Amino-5-(5-iodo-2-isopropyl-4-methoxy-phenoxy)-pyrimidin-2-yl]-isobutyramide, for example, exhibited a $pIC_{50}$ of approximately 7.8 for the $P2X_3$ receptor, and 7.4 for the $P2X_{2/3}$ receptor, using the above assay.

Example 9

In Vivo Assay for Asthma and Lung Function

BALb/cJ mice are immunized with a standard immunization protocol. Briefly, mice (N=8/group) are immunized i.p. with ovalbumin (OVA; 10 µg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

Example 10

Volume Induced Bladder Contraction Assay

Female Sprague-Dawley rats (200-300 g) were anesthetized with urethane (1.5 g/kg, sc). The animals were tracheotomized, and a carotid artery and femoral vein were cannulated for blood pressure measurement and drug administration, respectively. A laparotomy was performed and the ureters were ligated and transected proximal to the ligation. The external urethral meatus was ligated with silk suture and the urinary bladder was cannulated via the dome for saline infusion and bladder pressure measurement.

Following a 15-30 minute stabilization period the bladder was infused with room temperature saline at 100 µl/min until continuous volume-induced bladder contractions (VIBCs) were observed. The infusion rate was then lowered to 3-5 µl/min for 30 minutes before the bladder was drained and allowed to rest for 30 minutes. All subsequent infusions were performed as indicated except the lower infusion rate was maintained for only 15 minutes instead of 30 minutes. Bladder filling and draining cycles were repeated until the threshold volumes (TV; the volume needed to trigger the first micturition bladder contraction) varied by less than 10% for two consecutive baselines and contraction frequency was within 2 contractions for a 10 minute period following the slower infusion rate. Once reproducible TVs and VIBCs were established the bladder was drained and the animal was dosed with drug or vehicle (0.5 ml/kg, i.v.) 3 minutes prior to the start of the next scheduled infusion.

Example 11

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 µl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 12

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 13

Cold Allodynia in Rats with a Chronic Constriction Injury of the Sciatic Nerve

The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

Example 14

Cancer Bone Pain in C3H/HeJ Mice

The effects of compounds of this invention on bone pain are determined between Day 7 to Day 18 following intramedullary injection of 2472 sarcoma cells into the distal femur of C3H/HeJ mice.

Specifically, NCTC 2472 tumor cells (American Type Culture Collection, ATCC), previously shown to form lytic lesions in bone after intramedullary injection, are grown and maintained according to ATCC recommendations. Approximately $10^5$ cells are injected directly into the medullary cavity of the distal femur in anesthetized C3H/HeJ mice. Beginning on about Day 7, the mice are assessed for spontaneous nocifensive behaviors (flinching & guarding), palpation-evoked nocifensive behaviors (flinching & guarding), forced ambulatory guarding and limb use. The effects of compounds of this invention are determined following a single acute (s.c.) administration on Day 7-Day 15. In addition, the effects of repeated (BID) administration of compounds of this invention from Day 7-Day 15 are determined within 1 hour of the first dose on Days 7, 9, 11, 13 and 15.

Example 15

Determination of Pharmacokinetic Parameters

Male Crl:WI(GLx/BRL/Han)IGS BR (Hanover-Wistar) rats weighing 200-250 g were cannulated. Groups of three rats were used for each dose level of an experimental compound and one (1) non-cannulated rat was used as a vehicle control. Animals were allowed normal access to chow and water throughout the experiment. The prodrug (N-[4-amino-5-(5-iodo-2-isopropyl-4-methoxy-phenoxy)-pyrimidin-2-yl]-butyramide) was formulated as an aqueous solution or an aqueous suspension and a dose equivalent to (0.127 mmol) was administered orally by gavage. A blood sample (0.3 mL) was collected from the treated rats at 0.5, 1, 2, 3, 4, 6 and 8 hours after via the jugular cannula. A sample of at least 0.3 mL of blood was withdrawn from the untreated animals 3 h after dosing. After 24 h from dosing, as much blood as possible was collected from all treated and control animals. Potassium oxalate/NaF was added to the samples which were stored on ice during sampling procedure. The samples were spun in a refrigerated centrifuge at −4° C. as soon as possible and the plasma samples were stored −20° C. immediately after centrifugation and later transferred to a −80° C. freezer until analysis. The concentration of the prodrug and the parent compound (5-(5-Iodo-2-isopropyl-4-methoxy-phenoxy)-pyrimidine-2,4-diamine) was determined by hplc. Using the above procedure, a Cmax of 0 ng/ml and an AUC of 0 ng·h/ml were measured for the prodrug and a Cmax 61.9 ng/ml of and an AUC of 200 ng·h/ml were measured for the parent compound.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula (I):

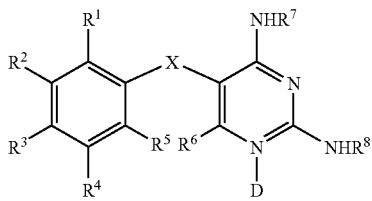

or a pharmaceutically acceptable salt thereof,
wherein:

X is:

—O—;

$R^1$ is: isopropyl;

$R^2$, $R^5$ and $R^6$ are hydrogen;

$R^3$ is alkoxy;

$R^4$ is halo or —C≡C—$R^a$— wherein $R^a$ is hydrogen;

one of $R^7$ and $R^8$ is hydrogen and the other is $R^9$, or both $R^7$ and $R^8$ are $R^9$: and each $R^9$ is independently:

—(C=O)—$R^d$;

—(O=)P(O$R^g$)$_2$;

—S(=O)$_2$O$R^g$; or a mono-, di- or tri-peptide, wherein $R^d$ is alkyl, alkoxy, amino, cycloalkyl, cycloalkylalkyl, aryl, arylalkyl, heteroaryl, heteroarylalkyl, heterocyclyl, cycloalkyloxy, cycloalkylalkyloxy, aryloxy, arylalkyloxy, heteroaryloxy, heteroarylalkyloxy, heterocyclyloxy, —(CH$_2$)$_p$—C(=O)—$R^e$, —(CH=CH)—C(=O)—$R^e$, or —CH(NH$_2$)—$R^f$;

wherein $R^e$ is hydrogen, hydroxy, alkyl, alkoxy, amino, cycloalkyl, cycloalkylalkyl, aryl, arylalkyl, heteroaryl, heteroarylalkyl, heterocyclyl, cycloalkyloxy, cycloalkylalkyloxy, aryloxy, aryl alkyloxy, heteroaryloxy, heteroarylalkyloxy or heterocyclyloxy;

p is 2 or 3;

$R^f$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl; and $R^g$ is hydrogen, alkyl, an alkali metal ion or an alkaline earth metal ion.

2. The compound of claim 1, wherein $R^4$ is iodo.

3. The compound of claim 1, wherein one of $R^7$ and $R^8$ is hydrogen and the other is $R^9$, $R^9$ is —(C=O)—$R^d$, and $R^d$ is alkyl, alkoxy, heteroaryl or heterocyclyl.

4. The compound of claim 1 wherein said compound is of the formula (II):

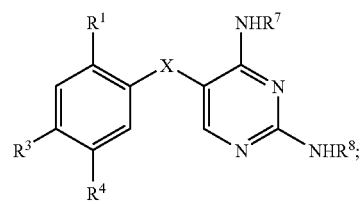

wherein X, $R^1$, $R^3$, $R^4$, $R^7$ and $R^8$ are as recited in claim 1.

5. The compound of claim 4, wherein $R^4$ is iodo.

6. The compound of claim 5 wherein one of $R^7$ and $R^8$ is hydrogen and the other is $R^9$, $R^9$ is —(C=O)—$R^d$, and $R^d$ is alkyl, alkoxy, heteroaryl or heterocyclyl.

7. A pharmaceutical composition comprising:
(a) a pharmaceutically acceptable carrier; and
(b) a compound of claim 1.

* * * * *